(12) United States Patent
Komatsu et al.

(10) Patent No.: US 6,512,578 B1
(45) Date of Patent: Jan. 28, 2003

(54) METHOD AND APPARATUS FOR SURFACE INSPECTION

(75) Inventors: Koichiro Komatsu, Tokyo (JP); Takeo Omori, Tokyo (JP); Toshiaki Kitamura, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/462,279

(22) PCT Filed: Jul. 9, 1998

(86) PCT No.: PCT/JP98/03076

§ 371 (c)(1),
(2), (4) Date: Feb. 22, 2000

(87) PCT Pub. No.: WO99/02977

PCT Pub. Date: Jan. 21, 1999

(30) Foreign Application Priority Data

Jul. 10, 1997 (JP) .............................. 9/200758
Aug. 29, 1997 (JP) .............................. 9/234505

(51) Int. Cl.[7] ................................ G01N 21/00
(52) U.S. Cl. ........................ 356/237.5; 356/237.2; 250/559.37
(58) Field of Search .................... 356/237.1, 237.2, 356/237.3, 237.4, 237.5, 237.6, 239.2, 239.3, 601, 603, 612, 614; 250/559.37, 559.38

(56) References Cited

U.S. PATENT DOCUMENTS

| | | | | |
|---|---|---|---|---|
| 3,825,351 A | * | 7/1974 | Seki et al. ............... | 356/237.1 |
| 3,902,807 A | * | 9/1975 | Fleming et al. .......... | 356/237.1 |
| 4,630,276 A | * | 12/1986 | Moran ...................... | 356/237.1 |
| 4,902,900 A | * | 2/1990 | Kamiya et al. ............ | 356/601 |
| 4,945,220 A | * | 7/1990 | Mallory et al. .......... | 250/201.3 |
| 5,235,400 A | * | 8/1993 | Terasawa et al. ........ | 356/237.1 |
| 5,510,892 A | * | 4/1996 | Mizutani et al. .......... | 356/614 |
| 5,535,005 A | * | 7/1996 | Mukherjee-Roy et al. .. | 356/601 |
| 5,583,632 A | * | 12/1996 | Haga ....................... | 356/237.1 |
| 5,587,794 A | * | 12/1996 | Mizutani et al. .......... | 356/614 |
| 5,682,244 A | * | 10/1997 | Barlow et al. ............. | 356/417 |
| 5,729,337 A | * | 3/1998 | Tanaka ..................... | 356/614 |
| 5,777,729 A | * | 7/1998 | Aiyer et al. .............. | 356/237.1 |
| 5,822,063 A | * | 10/1998 | Suzuki et al. ............. | 356/364 |
| 5,856,868 A | * | 1/1999 | Kato et al. ............... | 356/237.3 |
| 5,963,328 A | * | 10/1999 | Yoshida et al. .......... | 356/237.2 |

FOREIGN PATENT DOCUMENTS

| | | |
|---|---|---|
| JP | 55-164304 | 12/1980 |
| JP | 6-94631 | 4/1994 |
| JP | 8-75661 | 3/1996 |
| JP | 9-61365 | 3/1997 |

* cited by examiner

Primary Examiner—Hoa Q. Pham
Assistant Examiner—Sang H. Nguyen
(74) Attorney, Agent, or Firm—Oliff & Berridge, PLC

(57) ABSTRACT

A surface inspection apparatus of the present invention comprises: an illumination optical system 100 which is fixed at a first predetermined angle with respect to a wafer 3 and which irradiates a substantially parallel illuminating light toward the entire surface of the wafer 3; an image pickup device 6 which is fixed at a second predetermined angle with respect to the wafer 3 and which receives diffracted light or scattered light from the wafer 3 and projects an image of the wafer; and an image processing apparatus 7 which performs a macro inspection by taking the image signal generated by the image pickup device 6 and carrying out image processing, and is further provided with a plurality of interference filters F1~F4 to enable the variable setting of the wavelength of the illuminating light from the illumination optical system 100. In this apparatus, macro inspections can be carried out efficiently on a variety of objects while apparatus such as the illumination apparatus and the image projection apparatus are maintained in fixed positions.

26 Claims, 11 Drawing Sheets

METHOD AND APPARATUS FOR SURFACE INSPECTION

TECHNICAL FIELD

The present invention relates to technology for performing inspection of surfaces of substrates used in the manufacture of liquid crystal devices or semiconductor wafers used in the manufacture of ICs, and in particular relates to an apparatus and method for performing so-called macro inspections in which the entire surface of the object is examined.

BACKGROUND ART

The macro inspection of the surfaces of the substrates used in the manufacture of liquid crystal devices and the semiconductor wafers used in the manufacture of ICs (hereinafter these items may also be described as the 'object') refers to a visual inspection of the entire surface of the object. This inspection is performed to detect scratches or marks on the surface of the substrate or wafer, irregularities in the resist coating, or defects arising during the photolithography process. In conventional macro inspections, a spot light type white diffuse light source illuminates the object being rotated, and visual judgement by an examiner is performed to inspect the above-mentioned defects.

However, visual judgment by an examiner results in a variation in the level of inspection due to factors such as the difference in technical skill level between individual examiners and the physical condition of the examiner. This results in problems such as inefficiency and unstable inspection results. Furthermore, in the manufacture of substrates for liquid crystal devices and of wafers for ICs, because any surface contamination must be avoided, inspection processes performed by humans, which are one of the major causes of dust contamination, need to be avoided as much as possible.

As a result of the above-described situation, automated macro inspection processes have been proposed, such as the apparatus presented in Japanese Patent Application, Second Publication No. Hei 6-8789. In this apparatus, the surface of a wafer is illuminated with light and the reflected light therefrom is received via an ITV camera, and a surface defect inspection on the object is performed by comparing the reflected light image with a pre-recorded reflected light image of an object without defects. Because the field of view of the camera is smaller than the object, the object can be moved for inspection of the whole of the whole of the object. Furthermore, in this apparatus, in order to enable inspection under various illumination angles with respect to the object surface, the ITV camera is held in a stationary position and the angle of the object is varied.

However with the above type of surface inspection apparatus, a mechanism for setting the illumination angle is required, and when the mechanism is activated, dust may be generated by the moving parts of the mechanism, leading to the possibility of unwanted contamination of the surface of the object. The apparatus proposed in the aforementioned Japanese Patent Application performs macro inspections by using the light directly reflected off the surface of the object, and the camera is located so that the incident angle of the irradiated light on the surface of the object is equal to the reflection angle of the reflected light.

However, recently, the use of diffracted light or scattered light generated in accordance with the repeating pattern on the surface of the object has been investigated for use in surface inspection. In such a case, because the reception angle of the light from the object will vary due to factors such as the pattern pitch of the object, it is necessary to adjust the illumination angle of the illumination apparatus and the light reception angle of the image pick-up camera. Consequently, this case also requires a mechanism for adjusting the angles of illumination and reception, which generates dust and leads to the problem of unwanted contamination of the surface of the object.

In another case, Japanese Patent Application, First Publication No. Hei 8-75661 proposes an automatic inspection apparatus which is configured so that light from a light source is irradiated on to the object such as a wafer, and detection is performed by a single light reception optical system. With such an inspection apparatus, in the case where diffracted light from the object is to be detected, the diffraction angle will vary depending on the pattern pitch. Therefore, with wafers such as memory elements in which the elements are formed in a uniform pitch across the entire surface of the wafer, the inspection can be performed with a single measurement. However, in the case of CPU or ASIC (Application Specified IC) wafers where a variety of different types of elements are grouped together in different regions, the pattern pitch will differ for each of the regions, and therefore portions of the surface cannot be examined because no diffracted light is generated. Moreover, when an inspection is attempted on an object in which the pattern has been resist coated, the amount of diffracted light will vary considerably because the interference caused by the resist film will be heavily influenced by irregularities in the thickness of the film. Therefore, even thickness irregularities which have almost no effect on the process will be sufficient to cause the detection of a defect. Cases where the thickness of the resist is asymmetrical are particularly problematic, because the diffracted light image is very likely to develop irregularities and it is almost impossible to obtain a reliable inspection.

DISCLOSURE OF THE INVENTION

It is an object of the first embodiment of the present invention to provide a surface inspection apparatus which is able to efficiently carry out macro inspections on a variety of objects without requiring the variable adjustment of the illumination angle, the surface angle of the object, or the light reception angle for the light reception apparatus or image projection apparatus, that is, by maintaining the illumination apparatus and the image projection apparatus in fixed positions.

In order to achieve the above object, a first surface inspection apparatus according to the present invention (also referred to as a macro inspection apparatus) is characterized by comprising an illumination apparatus which is fixed in a position facing the object at a first predetermined angle with respect to the object and which irradiates an illuminating light beam which is a substantially parallel light beam, on to the inspection region of the object; an image projection apparatus which is fixed in a position facing the object at a second predetermined angle with respect to the object and which receives the diffracted light or scattered light generated from the illumination of the object by the aforementioned illuminating light beam and creates an image for the object; an image processing apparatus which is connected to the image projection apparatus and which takes the image signal obtained by the image projection apparatus and performs an inspection of the aforementioned inspection region by carrying out certain image processing; and a wavelength alteration member which is positioned within the optical path of the aforementioned illuminating light beam for altering the wavelength of the illuminating light. The operation of the apparatus may also be automated.

With a surface inspection apparatus of this construction, the wavelength of the illuminating light beam can be varied using the wavelength alteration member. Therefore, highly efficient macro inspection can be achieved by setting the wavelength so that the direction of the diffracted light or scattered light generated from the inspection region of the object coincides with the light reception direction of the image projection apparatus. Thus with this macro inspection apparatus, the illumination apparatus and the image projection apparatus can be fixed, making the provision of conventional moving mechanisms for altering the orientation of the illumination and image projection apparatus unnecessary, and hence reducing the generation of unnecessary dust and suppressing contamination of the object.

The illumination apparatus preferably has a diffuse light source and an optical member for converting the light from the light source into a substantially parallel light beam The aforementioned wavelength alteration member is preferably positioned between the diffuse light source and the optical member. In this situation, it is preferable for the optical member to have a concave mirror with the diffuse light source positioned at the focal point thereof. By using a concave mirror in this manner, the problem of chromatic aberration does not arise even in the case of illumination with white light.

Furthermore, for the same reasons, it is preferable for the image projection apparatus to have a concave mirror for converging the diffracted light or scattered light from the object, and an image pickup device for projecting an image of the object based on the converged light from the concave mirror.

The illumination apparatus can also have a linear diffuse light source and a cylindrical lens positioned facing along the line of the linear diffuse light source. In such a case, from the light from the linear diffusion source, the cylindrical lens generates a light beam which is substantially parallel in at least one direction and then illuminates the object. This type of construction allows the production of small scale, compact apparatuses at low cost.

The setting of the wavelength by the wavelength alteration member is carried out in the manner described below. In the case where the aforementioned first predetermined angle is represented by an angle of $\theta i$ with respect to a line perpendicular to the surface of the object, and the second predetermined angle is represented by an angle of $\theta d$ with respect to a line perpendicular to the surface of the object, then the wavelength $\lambda$ of the illuminating light beam is set so as to satisfy the following formula (1).

$$(\sin \theta i - \sin \theta d) = n \cdot \lambda / p \tag{1}$$

(n: order of diffracted light undergoing image projection, p: pattern pitch of the surface of the object)

If the wavelength $\lambda$ of the illuminating light beam is set according to the above formula, then the image projection apparatus is able to efficiently capture diffracted light of order n, and the macro inspection utilizing this diffracted light can also be carried out efficiently.

In the case where a macro inspection is performed by capturing scattered light (rather than diffracted light) with the image projection apparatus, the setting of the wavelength by the wavelength alteration member is carried out in the manner described below. In the case where the first predetermined angle is represented by an angle of $\theta i$ with respect to a line perpendicular to the surface of the object, the second predetermined angle is represented by an angle of $\theta d$ with respect to a line perpendicular to the surface of the object, and the wavelength of the illuminating light beam which is set by the wavelength alteration member is represented by $\lambda$, then the wavelength $\lambda$ of the illuminating light beam is set by the wavelength alteration member so that the value of $\theta d$ satisfies the requirement $\theta d' < \theta d < \theta d''$, where $\theta d'$ is determined by the formula (2), and $\theta d''$ is determined by the formula (3).

$$(\sin \theta i - \sin \theta d') = n \cdot \lambda / p \tag{2}$$

$$(\sin \theta i - \sin \theta d'') = (n+1) \cdot \lambda / p \tag{3}$$

(n: order of the diffracted light generated from the illuminating light beam, p: pattern pitch of the surface of the object).

If the wavelength $\lambda$ of the illuminating light beam is set according to the above formulae, then the image projection apparatus is positioned between the direction of diffracted light of order n and the direction of diffracted light of order (n+1), meaning that no diffracted light will enter the image projection apparatus and only scattered light will be received. Consequently, macro inspection utilizing the scattered light can be carried out efficiently.

In order to achieve the above object, a second surface inspection apparatus according to the present invention, as shown in FIG. 9 comprises a first light reception optical system for receiving a first light beam (diffracted light or scattered light) from the surface; a second light reception optical system for receiving a second light beam (diffracted light or scattered light) from the surface; a first image processing apparatus for processing the image of the surface generated by the first light reception optical system; a second image processing apparatus for processing the image of the surface generated by the second light reception optical system, and a central computing device for detecting the condition of the surface by processing the information generated by the first and second image processing apparatus.

The second embodiment of the present invention is able to provide a surface inspection apparatus and a surface inspection method which enable highly reliable inspections to be performed regardless of the condition of the surface.

With the above construction, a first light beam (diffracted light or scattered light) from the surface is received by the first light reception optical system, and the surface image thus produced is processed by the first image processing apparatus. In the same way, a second light beam (diffracted light or scattered light) from the surface is received by the second light reception optical system, and the surface image thus produced is processed by the second image processing apparatus. Then, the condition of the surface is detected by processing the information generated by the two image processing apparatuses using the central computing device. The provision of the central computing device makes it possible to detect surface conditions which could not be distinguished from only a single set of information, by enabling the superimposition of two sets of data and subsequent addition or subtraction operations to be performed.

In such a case, it is also possible to provide an illumination optical system for illuminating the surface, and then positioning the optical axes of the first and second light reception optical systems in a substantially symmetrical manner with respect to the optical axis of the illumination optical system.

Furthermore, it is possible to project the illuminating light beam obliquely, and to position the light reception optical systems symmetrically for receiving the diffracted light from the intersecting pattern formed on the surface. Alternatively, it is possible to project the illuminating light beam substantially perpendicularly on to the surface, and to position the light reception optical systems symmetrically for receiving diffracted light from the pattern of order ±n (where n is an integer).

With such an apparatus, in order to enable reception by the aforementioned first and second light reception optical systems of the diffracted light or scattered light generated in accordance with the structure of a body located on the aforementioned surface, the surface incorporating the optical axis of the first light reception optical system and the normal line H of the surface may intersect with the surface incorporating the optical axis of the second light reception optical system and the normal line H of the surface.

With such a construction, a light reception optical system is provided for which the optical axis lies within the intersecting surfaces, and so for example the two different directions of diffracted light generated from a semiconductor substrate, in which a pair of line and space patterns intersect one another, can be received simultaneously. Depending on the process, there are cases in which the direction of the diffracted light produced is not necessarily constant. This is because in memory elements and the like, line and space patterns are frequently positioned so as to intersect, and the diffracted light will typically be generated in a direction perpendicular to the lines. In such cases, with light reception systems which can accommodate only one direction of diffracted light, the wafer needs to be rotated to enable the diffracted light to be captured. This can result in an undesirable reduction in processing time, but with a construction of the present invention the two directions can be measured simultaneously. The patterns do not necessarily intersect orthogonally and so the light reception systems should be positioned in accordance with the pattern, in the direction of the generated diffracted light. However, orthogonal intersections are frequent, as in the case of a pair of line and space patterns which intersect orthogonally. In such cases, light reception optical systems having optical axes within the orthogonally intersecting surfaces should be provided.

A surface inspection method according to the present invention comprises an illumination step for illuminating the surface to be measured; a first light reception step for receiving a light beam (diffracted light or scattered light) of a first direction produced at the surface which has been illuminated via the illumination step; a second light reception step for receiving a light beam (diffracted light or scattered light) of a second direction produced at the surface which has been illuminated via the illumination step; a first image processing step for processing the image of the surface generated by the first light reception step; a second image processing step for processing the image of the surface generated by the second light reception step; and a step for detecting the condition of the surface by processing the information generated by the first and second image processing steps.

With such a construction, the surface is illuminated at the illumination step which produces diffracted light or scattered light. Because steps are provided for receiving light of both the first and second directions, a plurality of images are obtained. An image-processing step is provided for each of the different light directions therefore, for example, the plurality of images can be combined and then processed centrally.

With this method, using an example in which the pattern formed on the surface is a line and space pattern with an associated periodicity, and the aforementioned first and second light beams are a diffracted light beam of a first direction and a diffracted light beam of a second direction respectively, then each of the directions can be set as those directions substantially perpendicular to the lines of the aforementioned line and space patterns. For semiconductor devices, frequently the line and space patterns are formed so as to intersect orthogonally, but if the first and second directions are chosen so as to be substantially perpendicular with respect to the lines of the respective line and space patterns, then the diffracted light from each pattern can be received at the first and second directions.

Furthermore, with the method of the present invention, the aforementioned first and second directions could also be set to the traveling direction of diffracted light of order plus 1 and diffracted light of order minus 1 from the aforementioned line and space patterns. In such a case, the first and second directions correspond with the direction of the diffracted light of order ±1, enabling information to be obtained on symmetrical directions related to the surface.

In a second surface inspection method according to the present invention, the wavelength of the illuminating light beam is altered, the surface is illuminated with the illuminating light beam of altered wavelength, and an inspection of the surface is performed based on reflected light from the surface.

With such a method, illumination with an illuminating light beam of altered wavelength provides a plurality of images which can, for example, be combined and a surface inspection can then carried out centrally.

A third surface inspection apparatus according to the present invention comprises an illumination apparatus which is positioned in a predetermined position relative to the surface and which illuminates the surface with an illuminating light beam; a wavelength alteration member which can be moved in and out of the optical path of the illuminating light beam and which alters the wavelength of the illuminating light beam; and a light reception apparatus which is positioned in a predetermined location relative to the surface and which receives light from the surface produced by illumination with the wavelength altered illuminating light beam. With this type of apparatus, a plurality of images are obtained by illumination with the illuminating light beam of altered wavelength, and they can, for example, be combined and a surface inspection carried out centrally.

Furthermore, a method for assembling a surface inspection apparatus according to the present invention involves positioning the illumination apparatus, which illuminates the surface with an illuminating light beam, in a predetermined location relative to the surface, positioning the wavelength alteration member, which alters the wavelength of the illuminating light beam, so as to enable movement in and out of the optical path of the illuminating light beam, and positioning the light reception apparatus, which receives light from the surface produced by illumination with the wavelength altered illuminating light beam, in a predetermined location relative to the surface.

BEST MODE FOR CARRYING OUT THE INVENTION

As follows is a description of the preferred embodiments of the present invention.

[First Embodiment]

Figure 1:
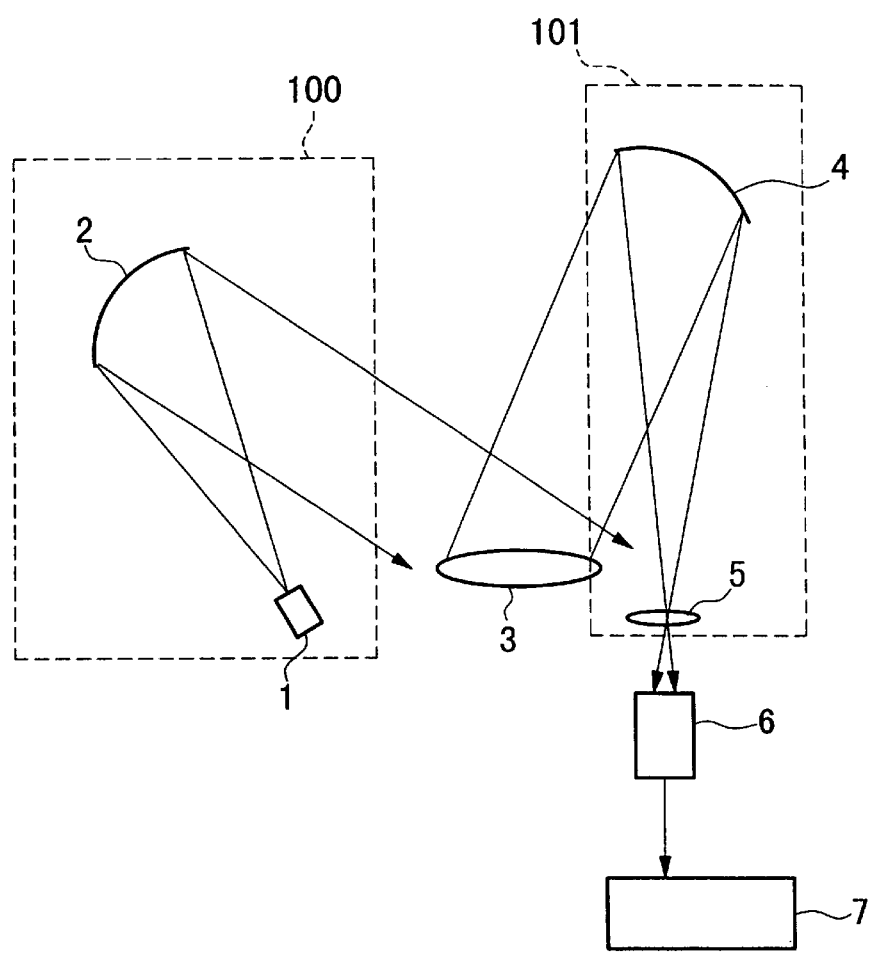
FIG. 1 is a schematic diagram showing a surface inspection apparatus according to a first embodiment of the present invention.

FIG. 1 shows a schematic construction of a surface inspection apparatus according to a first embodiment of the present invention, wherein the apparatus comprises: an illumination optical system 100 for irradiating a parallel illuminating light beam on to the surface of a wafer (object) 3, a light reception system 101 for receiving diffracted light or scattered light from the wafer 3, an image pickup device (imaging camera) 6, and an image processing apparatus 7.

The illumination optical system 100 is constructed of a light source 1 and a concave mirror 2. The light source 1 is located at the focal point of the concave mirror 2. The diffuse light from the light source 1 is converted to a parallel light beam by the concave mirror 2, and is then illuminated on to the wafer 3. The concave mirror 2 has an aperture which is sufficiently large to enable illumination of the entire surface of the wafer 3, and this makes it possible for the entire surface of the wafer 3 to be simultaneously illuminated by the parallel illuminating light beam. The light source 1 comprises a white light source such as a halogen lamp and an interference filter for limiting the wavelength bandwidth of the illuminating light. The interference filter functions as a band pass filter by transmitting light of a predetermined wavelength bandwidth, and selection of the wavelengths being generated from the light source 1 can be achieved by switching the interference filter, either manually or by remote operation, with any of a plurality of interference filters which transmit light of different wavelength bandwidths.

Figure 2:
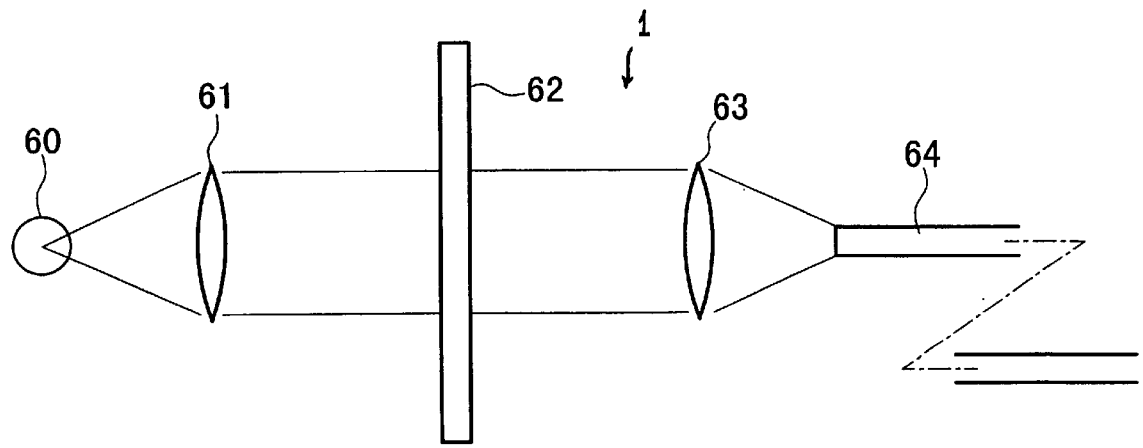
FIG. 2 is a schematic diagram showing an example of a wavelength variable illumination apparatus for use in a surface inspection apparatus.
Figure 3:
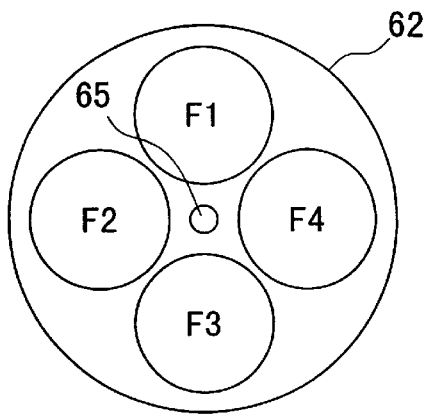
FIG. 3 is a front elevation showing a filter selection mechanism of a wavelength variable illumination apparatus.
Figure 4:
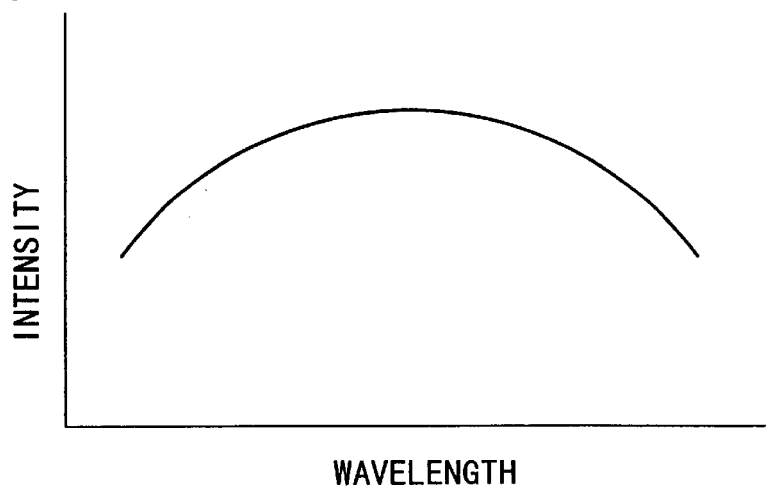
FIGS. 4 and 5 are graphs illustrating the operation of a wavelength variable illumination apparatus.
Figure 5:
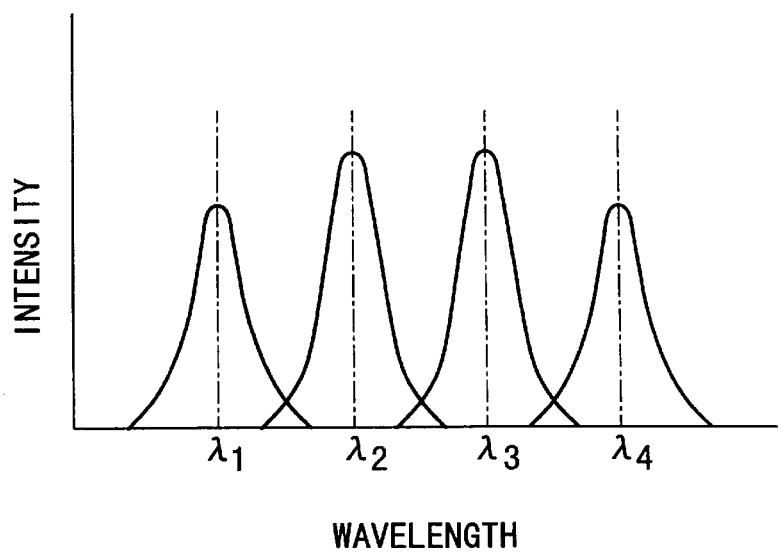

FIG. 2 shows a specific example of a wavelength variable light source 1. The light source 1 of this example is provided with a white light source 60 such as a halogen lamp, a lens 61 for converting the light from the white light source 60 into a parallel light beam, and a lens 63 for converging the parallel light beam from the lens 61 and then introducing the light into an optical fiber 64, wherein the light is then irradiated from the other end of the optical fiber 64 in the direction of a reflective mirror 2. A lens may also be provided between the optical fiber 64 and the reflective mirror 2. A rotary holder 62, which supports a plurality (four in this example) of wavelength selection filters F1~F4 as shown in FIG. 3, is positioned between the lenses 61, 63, and by rotating the rotary holder 62 about a rotational axis 65 any of the wavelength selection filters F1~F4 can be placed in the optical path. Each of the wavelength selection filters F1~F4 has a different wavelength transmission band, and will convert white light similar to that shown in FIG. 4 into a light beam of narrow frequency bandwidth represented by one of the central peaks $\lambda 1$~$\lambda 4$ shown in FIG. 5. The rotation of the holder 62 can be performed either manually or automatically. The wavelength variable light source of the present invention is not limited to the example shown in FIG. 2, and light sources provided with devices such as wavelength variable lasers, spectral prisms or diffraction gratings can also be used.

The light reception system 101 receives the diffracted light or scattered light generated at the wafer 3 upon illumination of the wafer 3 in the manner described above. The light reception system 101 comprises a concave mirror 4 of a sufficiently large aperture to capture diffracted light or scattered light from the entire surface of the wafer 3, and a light reception lens 5 for imaging the light converged by the concave mirror 4. The light reception lens 5 produces the image on the image pickup device 6, and the image pickup device 6 projects an image of the diffracted light or scattered light from the wafer 3.

The wafer image projected by the image pickup device 6 is sent to the image processing apparatus 7, and macro inspections such as surface defect inspections are then carried out by comparison of the wafer image with a pre-recorded image of a wafer without defects.

In this embodiment the light source 1 is positioned in the vicinity of the front focal point of the concave mirror, and the wafer 3 is positioned in the vicinity of the rear focal point of the concave mirror 4, creating a reflective telemetric optical system which utilizes concave reflective mirrors. By using concave mirrors in the optical system, problems of chromatic aberration do not arise and highly accurate inspections are possible.

In the following, a description of a sample macro inspection of a wafer 3 using a surface inspection apparatus of the construction described above is explained. First the wafer 3 is positioned at the inspection location shown in FIG. 1 by a carrying mechanism which is not shown in the diagrams. An interference filter is then chosen for the light source 1 in accordance with the location of the wafer and the type of inspection (a macro inspection by scattered light, or a macro inspection by diffracted light) being performed. In this embodiment, both the illumination optical system 100 and the light reception system 101 are at fixed locations. In addition, because the incident angle of the illuminating light beam from the illumination optical system 100 on to the wafer 3 is always constant, and moreover because the diffraction angle of the diffracted light entering the light reception system 101 is also always constant, the selection of the interference filter is performed so as to ensure light for the desired inspection enters the light reception system 101.

Figure 7:
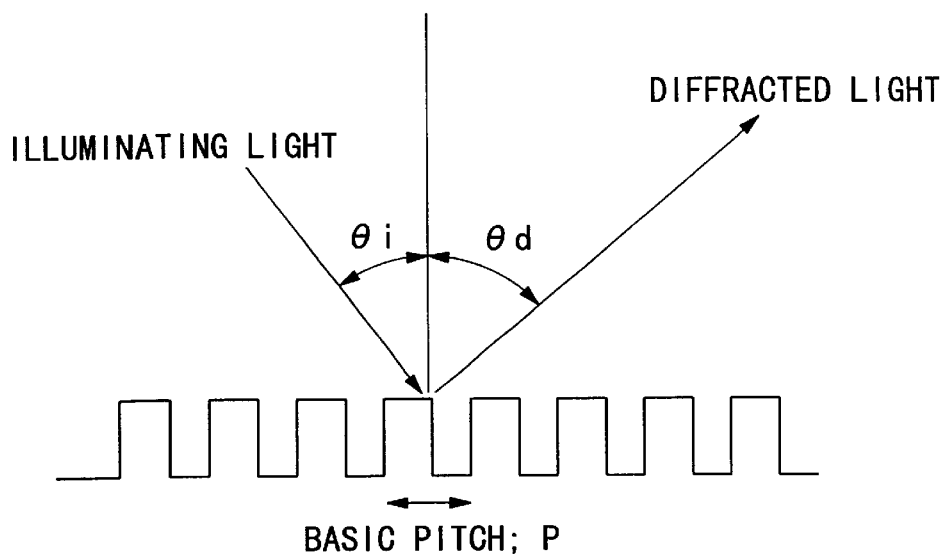
FIG. 7 is an explanatory diagram showing the relationship between the illuminating light irradiated on to a wafer and the diffracted light.

This point is described in further detail below with reference to FIGS. 7 and 8. As shown in FIG. 7, when the surface of the wafer 3 has a repeating pattern of basic pitch p, the relationship between the incident angle θi of the illuminating light beam and the diffraction angle θd of the diffracted light is represented by the formula (4).

$$(\sin θi - \sin θd) = n·λ/p \quad (4)$$

(λ: wavelength of the illuminating light beam n: order of the diffracted light undergoing imaging)

Consequently, by positioning the illumination optical system 100 so that illumination of the wafer 3 by a parallel light beam will occur at an incident angle of θi, and positioning the light reception system 101 so that the concave mirror 4 will be located facing the reflection angle θd of the diffracted light, diffracted light of order n will be able to be received at maximum efficiency by the light reception system 101 in the case where the illuminating light beam is of wavelength λ. In the present embodiment, the illumination optical system 100 and the light reception system 101 are at fixed locations, and so the interference filter is chosen to give a wavelength λ which for those fixed locations will enable diffracted light of order n to be received at maximum efficiency by the light reception system 101.

There are also cases where macro inspections are performed by receiving scattered light by the light reception system 101. In such cases, as shown in FIG. 8, the wavelength λ of the illuminating light beam is set so that the concave mirror 4 of the light reception system 101 is positioned at a location between the diffraction angle θd' of diffracted light of order n, and the diffraction angle θd" of diffracted light of order (n+1). Specifically, because the diffraction angle θd' of diffracted light of order n is determined by the formula (5), and the diffraction angle θd" of diffracted light of order (n+1) is determined by the formula (6), the wavelength λ of the illuminating light beam is set by the wavelength alteration member so that the angle θd of the diffracted light irradiated on to the concave mirror 4 of the light reception system 101 satisfies the requirement θd'<θd<θd".

$$(\sin θi - \sin θd') = n·λ/p \quad (5)$$

$$(\sin θi - \sin θd") = (n+1)·λ/p \quad (6)$$

Figure 8:
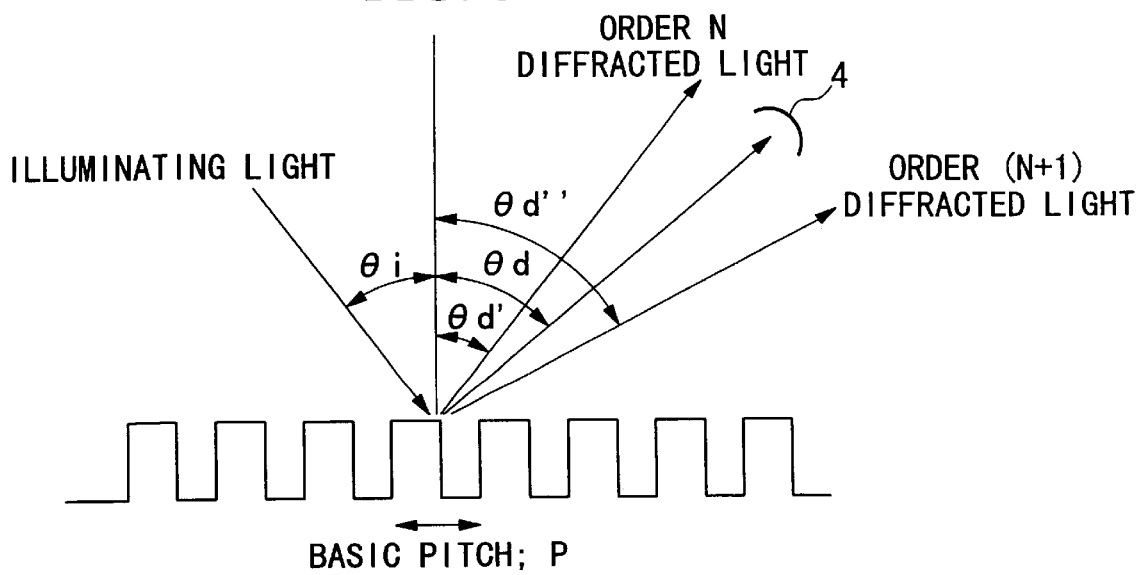
FIG. 8 is an explanatory diagram showing the relationship between the illuminating light irradiated on to a wafer, diffracted light of order n and (n+1), and the position of a concave mirror of a light reception system.

By carrying out selection of the wavelength λ in the manner described above, when the illuminating light beam of this wavelength is irradiated on to the wafer 3, then as shown in FIG. 8, diffracted light of order n is generated at an angle of θd', and diffracted light of order (n+1) is generated at an angle of θd", and because the concave mirror 4 of the light reception system 101 is positioned between the two angles, no diffracted light is captured by the light reception system 101, with only scattered light being received, which enables a very efficient macro inspection to be performed using scattered light.

Furthermore, it is also possible to set the wavelength λ of the illuminating light beam so that diffracted light of order (n+1) is received by the light reception system 101. Consequently with the present embodiment, macro inspections using diffracted light of order n, as well as macro inspections using diffracted light of order (n+1) are possible. Macro inspections using diffracted light of other orders are of course also possible.

Moreover, macro inspections can also be carried out using results from at least one of either diffracted light or scattered light, or at least one of a plurality of diffracted light beams of different orders.

As described above, the diffracted light or scattered light captured by the light reception system 101 is converged on to the light reception lens 5 by the concave mirror 4, and converted to an image on the image pickup device 6 by the light reception lens 5. The image information projected by the image pickup device 6 is sent to the image processing apparatus 7 where a macro inspection is performed automatically by comparing the image with the image of a wafer without defects.

It is also possible to provide a rotational support mechanism to the apparatus which supports the wafer 3 at the inspection position to carry out adjustments of the rotational position of the wafer 3. With such an apparatus, because the wafer 3 can be rotated in correspondence with the direction of the pattern or defects on the wafer 3, the direction of the illuminating light beam, the intensity of the diffracted light, and the direction of the generated scattered light, it is possible to improve the efficient of the surface inspection.

In the embodiment described above concave mirrors were used, but reflective Fresnel zone plates could also be used instead of the mirrors. Moreover, a dioptric system using lenses, which has been corrected for chromatic aberration, could also be used.

[Second Embodiment]

Figure 6:
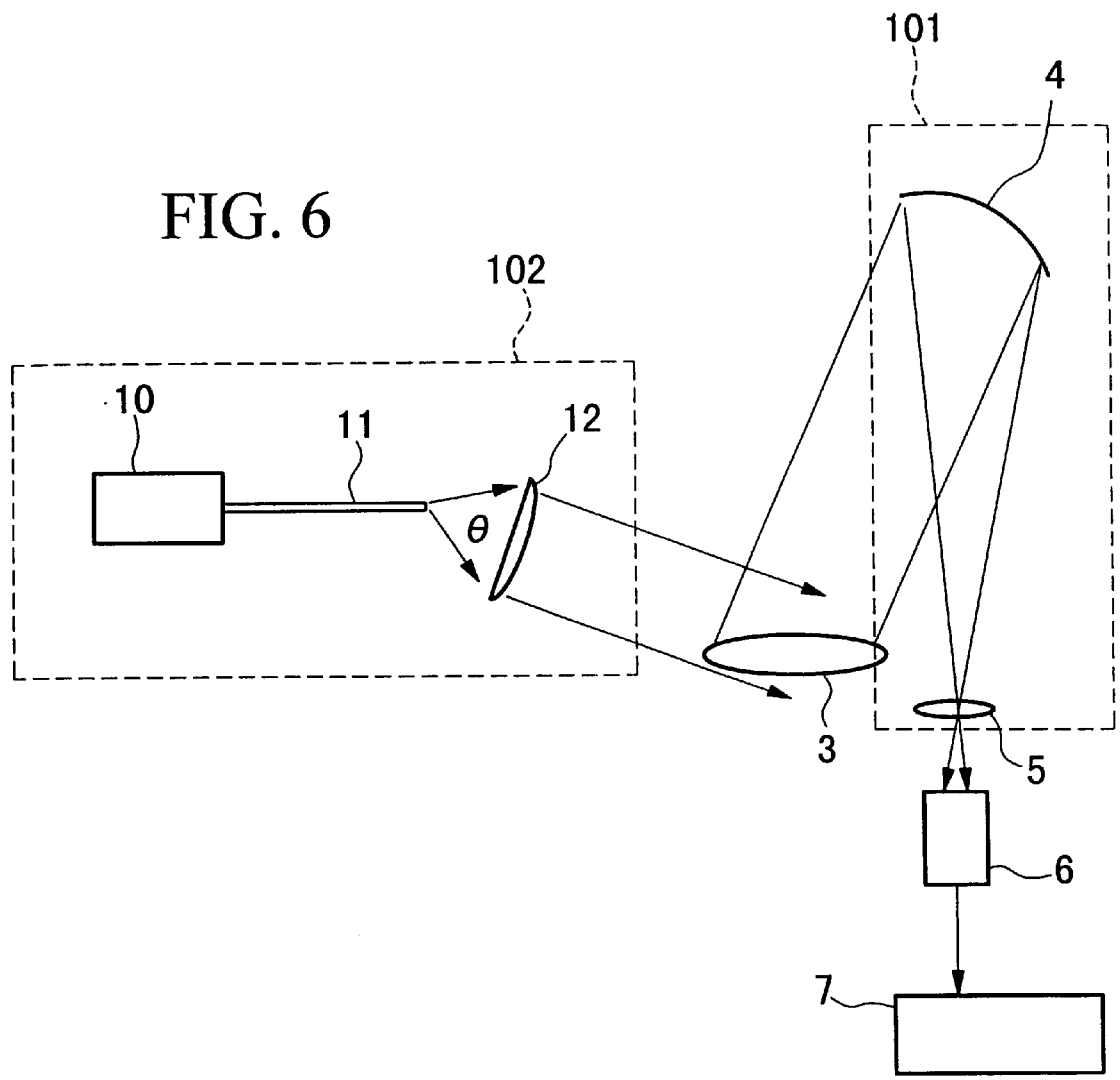
FIG. 6 is a schematic diagram showing a surface inspection apparatus according to a second embodiment of the present invention.

Next is a description of a second embodiment of a surface inspection apparatus according to the present invention, with reference to FIG. 6. In the apparatus of this embodiment, those sections which are identical with the corresponding sections of the apparatus of the first embodiment are denoted by the same reference symbols, and description thereof is omitted. The apparatus of this embodiment comprises: an illumination optical system 102, a light reception system 101, an image pickup device 6, and an image processing apparatus 7, and only the illumination optical system 102 differs from that of the apparatus of the first embodiment.

The illumination optical system 102 comprises a light source 10, an optical fiber light guide system 11, and a cylindrical lens 12, and the wafer 3 is illuminated with a light beam capable of illuminating the entire surface of the wafer 3. The light source 10 comprises a white light source such as a halogen lamp and an interference filter for limiting the illumination wavelength band, as shown in FIG. 2. The construction can be identical to that described for the first embodiment.

The optical fiber light guide system 11 is positioned so that one end (the incident end) faces, and captures the illuminating light beam from the light source 10, and the other end (the emission end) is arranged in a one-dimensional linear type configuration. As a result, the light beam irradiated from the other end of the optical fiber light guide system 11 is a diffuse beam which spreads out at a divergence angle θ within a plane parallel with the paper surface of FIG. 6, and becomes a light source with a width, in the direction perpendicular to the paper surface, of the linear length of the fiber.

The other end of this optical fiber light guide system 11 is positioned at the rear focal point of the cylindrical lens 12, and the diffuse light beam irradiated from this other end of the optical fiber light guide system 11 is converted by the cylindrical lens 12 into a substantially parallel light beam within a plane parallel to the paper surface. Consequently, a light beam which is at least within the plane parallel to the paper surface of FIG. 6 and which is similar to the parallel light beam generated by the telemetric optical system shown in the first embodiment is irradiated on to the entire surface of the wafer 3.

When the wafer 3 is illuminated with the illuminating light beam, the diffracted light or scattered light thus generated is captured by the light reception system 101, and then projected as an image by the image pickup device 6, with the image then being processed by the image processing apparatus 7 to complete the macro inspection. This process is identical with that described for the first embodiment and so the description is omitted here.

With a macro inspection apparatus of this type of construction, the illumination optical system can be of a small and compact construction, and moreover can be produced cheaply.

In both the first and second embodiments described above, the light source can also be constructed by combining a white light source and a spectrometer.

[Third Embodiment]

Figure 9:
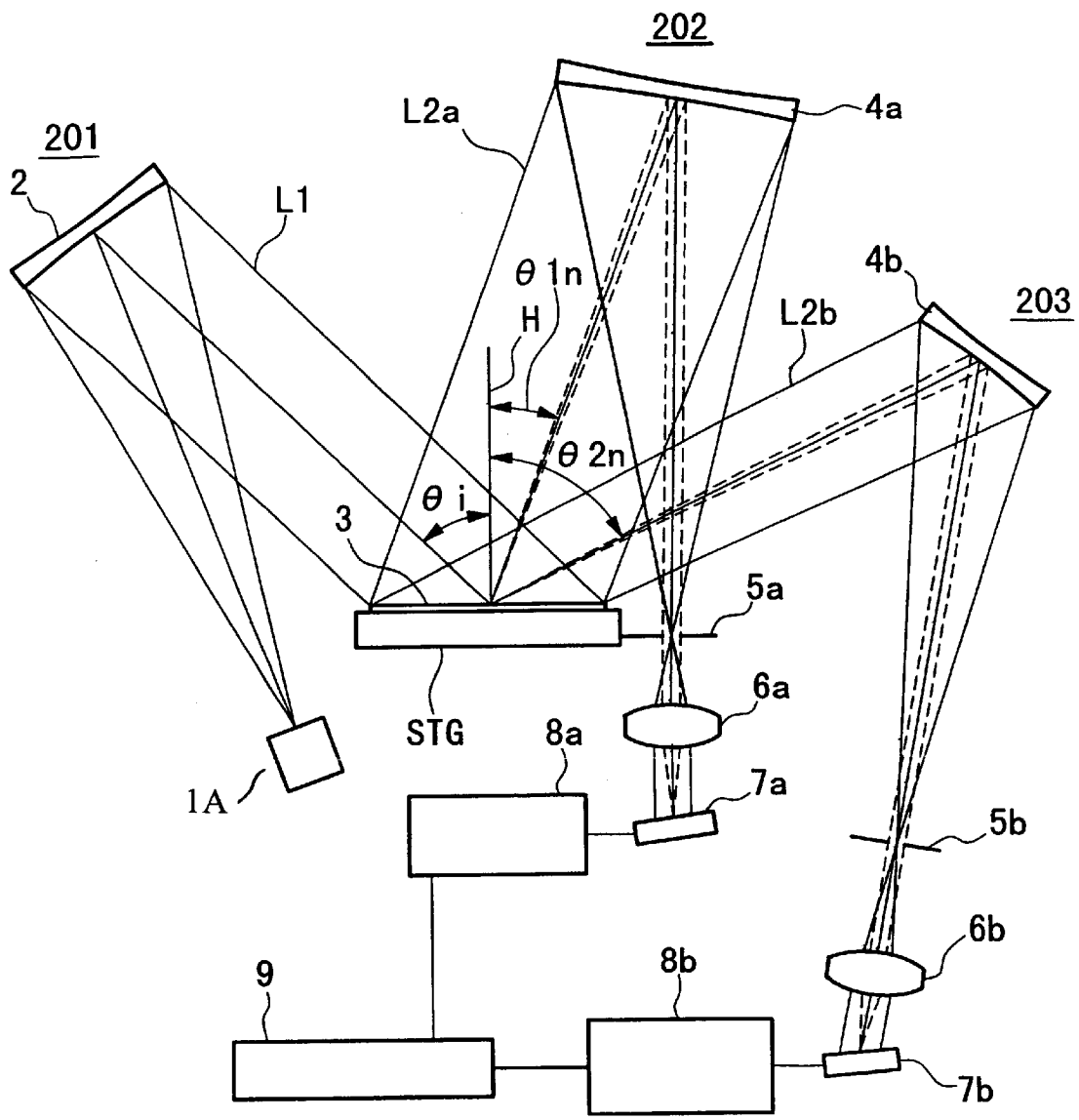
FIG. 9 is a side elevation of a surface inspection apparatus of another embodiment of the present invention.

FIG. 9 is a side elevation showing a third embodiment of the present invention. In FIG. 9, those construction elements which are identical with those of the previously described embodiments are denoted by the same reference symbols. In this embodiment, a plurality of light reception systems are provided in order to deal with a plurality of pitch patterns. An illumination optical system 201 is provided for illuminating a substrate 3 such as a wafer which is mounted on the substrate stage STG. A concave mirror 2 which functions as an illumination condenser mirror is positioned in the direction to generate irradiation of the substrate with the illuminating light beam at a predetermined incident angle θi relative to the substrate, and a light source 1A which generates substantially a monochromatic light beam is positioned at the focal surface of the mirror 2. The light source 1A differs from the light source 1 described above, and can be either a monochromatic or white light source for which the frequency can not be altered, or a wavelength variable light source such as the aforementioned light source 1. In the case where a wavelength variable light source such as that shown in FIG. 2 is used, then as described below, a variety of macro inspections can be efficiently carried out with the illumination angle, the surface angle of the object, and the light reception angle all maintained at fixed values.

In the present embodiment, the illumination optical system 201 incorporates the light source 1A and the concave mirror 2. The light beam generated from the light source 1A is converted to a substantially parallel light beam L1 by the illumination condenser mirror 2, and is then irradiated on to the substrate 3 at an incident angle of θi. In FIG. 9 the letter H represents the normal line of the substrate surface.

Of the patterns formed on the surface of the substrate 3, diffracted light of order n from the first pitch p1 travels out at an angle of θ1n relative to the normal line H of the substrate 3. This angle θ1n is termed the diffraction angle. For light of wavelength λ, the relationship between these values is represented by the following formula.

$$\sin \theta i + \sin \theta 1n = n\lambda/p1$$

Similarly, of the patterns formed on the surface of the substrate 3, the diffraction angle θ2n of diffracted light of order n from the second pitch p2 is represented by the following formula.

$$\sin \theta i + \sin \theta 2n = n\lambda/p2$$

The following is a description of the light reception system of the present embodiment. In FIG. 9, the first light reception optical system 202, which receives diffracted light from the first pitch pattern p1, comprises a concave mirror 4a which functions as a light reception mirror and which is positioned in the opposite direction to the direction of incident light L1 with respect to the normal line H of the substrate 3 at a diffraction angle of θ1n; a diaphragm 5a which is provided in the vicinity of the pupil for the light reception mirror 4a in the traveling direction of reflected light from the mirror 4a; an imaging lens 6a which is provided in the traveling direction of light which has passed through the diaphragm 5a; and an image pickup device 7a such as a CCD which is provided at a conjugate position with the surface of the substrate 3 with respect to the light reception mirror 4a and the imaging lens 6a.

The substrate 3 is generally tilted with respect to the optical axis of the light reception optical system, and hence has a swing angle, and so it is preferable for the image pickup device 7a to be tilted at a swing angle sufficient to satisfy the Shineproof condition. To describe the Shineproof condition further, for an optical system imaging a pattern from a surface A on to a surface B, in order for the surfaces A and B to satisfy the Shineproof condition, then within the meridional cross-section, if the point of intersection of the line extended from the surface A and the image principal plane of the optical system is termed H and the point of intersection of the line extended from the surface B and the image principal plane of the optical system is termed H', then the distance from the intersection point H to the optical axis will be equal to the distance from the intersection point H'l to the optical axis. When the Shineproof condition is satisfied, then a so-called swinging image relationship is established, and a light beam generated from any point on the surface A will be converged on to a corresponding point on the surface B. A detailed description of the Shineproof condition is given on pages 64–67 of "Hikarikiki no Kougaku I" JOEM by Hayami Yoshisada and the description is incorporated in this specification by reference.

The first light reception optical system 202 receives a first diffracted light beam L2a of diffraction angle θ1n from the substrate 3 at the light reception mirror 4a, and from the reflected light from this light beam, the diaphragm 5 located in the vicinity of the pupil for the light reception mirror 4a isolates only the diffracted light traveling in the direction of the aforementioned diffraction angle θ1n.

The isolated diffracted light forms an image of the diffracted light of order n from the first pitch p1 of the substrate 3 on the imaging surface of the image pickup device 7a using the imaging lens 6a. The thus formed image undergoes a photoelectric conversion at the imaging surface 7a and is converted into an electrical signal which corresponds with the optical intensity.

In an identical manner, the second light reception optical system 203, which receives diffracted light from the second pitch pattern p2 comprises a concave mirror 4b which functions as a light reception mirror and which is positioned in the opposite direction to the direction of incident light L1 at a diffraction angle of θ2n, a diaphragm 5b which is provided in the vicinity of the pupil for the light reception mirror 4b, an imaging lens 6b which is provided in the traveling direction of light which has passed through the diaphragm 5b, and an image pickup device 7b which is provided at a conjugate position with the surface of the substrate 3 so as to satisfy the Shineproof condition.

The operation of the second light reception optical system 203 is also identical with that of the first optical system. That is, an image is formed of the diffracted light of order n from the second pitch p2 of the substrate 3, and the image undergoes a photoelectric conversion at the imaging surface 7b and is converted into an electrical signal which corresponds with the optical intensity.

The electrical signals of the two images are transmitted to the respective image processing apparatus 8a, 8b which are connected electrically to the corresponding imaging surfaces 7a, 7b. By comparison of the images with the image of a defect free substrate already stored in the image processing apparatus 8a, 8b, any foreign matter adhered to the surface of the substrate 3, scratches on the substrate surface, or irregularities in the pattern are detected. The results obtained by the image processing apparatus 8a, 8b are processed as substrate defect data by a computer 9 which functions as a central computing device. The image processing apparatus 8a, 8b and the central computing device could also be combined into a single apparatus.

The light reception optical apparatus 202, 203 should preferably be configured so that a tilt adjustment mechanism, which is not shown in the diagrams, is used to set the apparatus at the direction of the corresponding diffraction angle $\theta 1n$, $\theta 2n$ of the pattern.

The present embodiment can be used effectively for the inspection of substrates such as ASICs in which there are regions which have different pitch patterns. This embodiment enables the simultaneous inspection of different pitch patterns, and so enables a greater device manufacture throughput.

The above description details the provision of a plurality of optical systems to deal with a plurality of pitch patterns (pitch p1 and pitch p2), but the apparatus of this embodiment can also be used for the capture and inspection of diffracted light of different orders from a single pitch pattern, such as diffracted light of order n and that of order (n+1) for example. In such a case, one of the diffracted light beams L2a, L2b would represent diffracted light of order n, and the other would represent diffracted light of order (n+1). By examining a plurality of diffracted light beams of different order from a single pattern, the accuracy and reliability of the inspection is improved.

[Fourth Embodiment]

Figure 10:
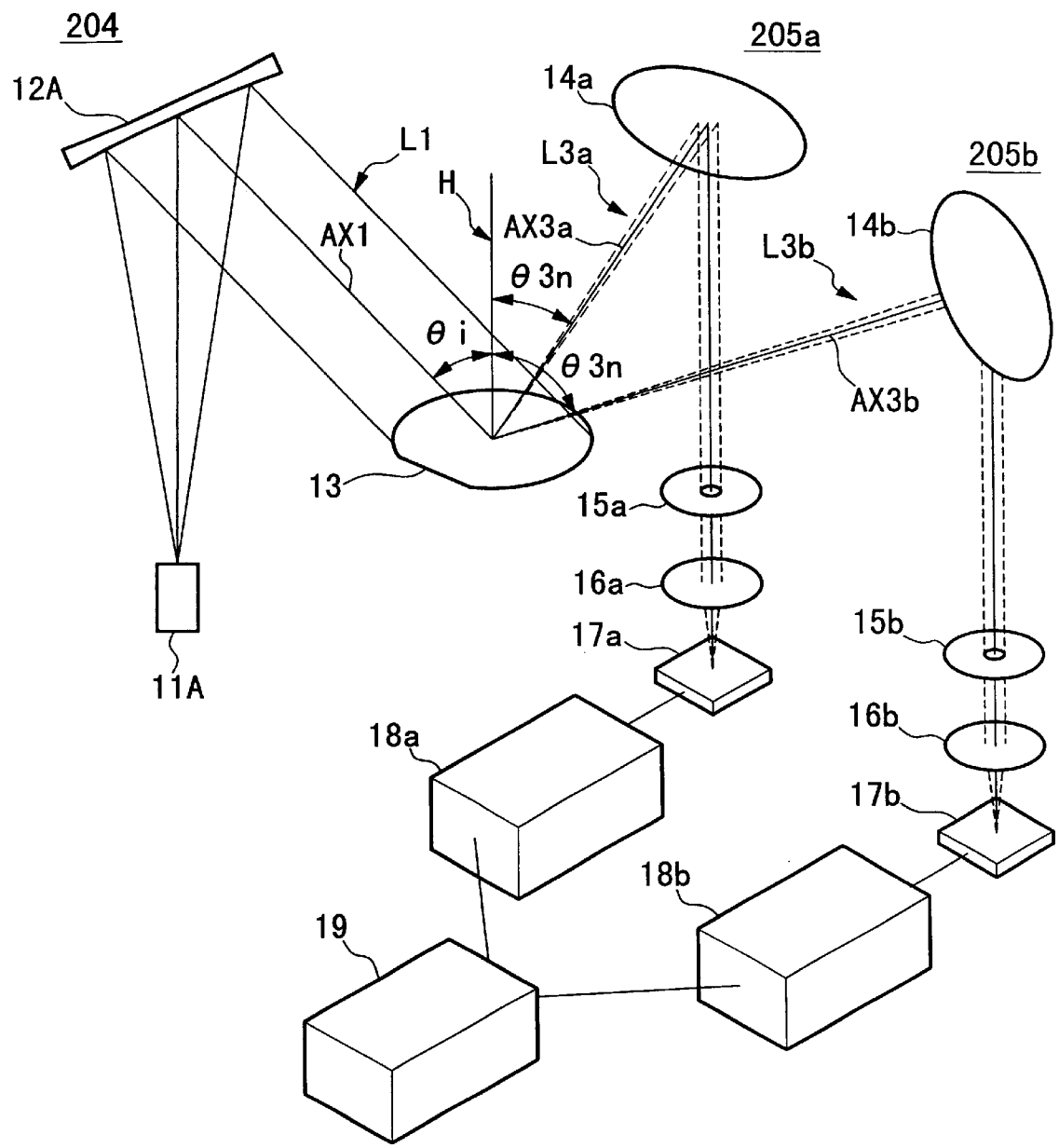
FIG. 10 is a perspective view of a surface inspection apparatus of yet another embodiment of the present invention.
Figure 11:
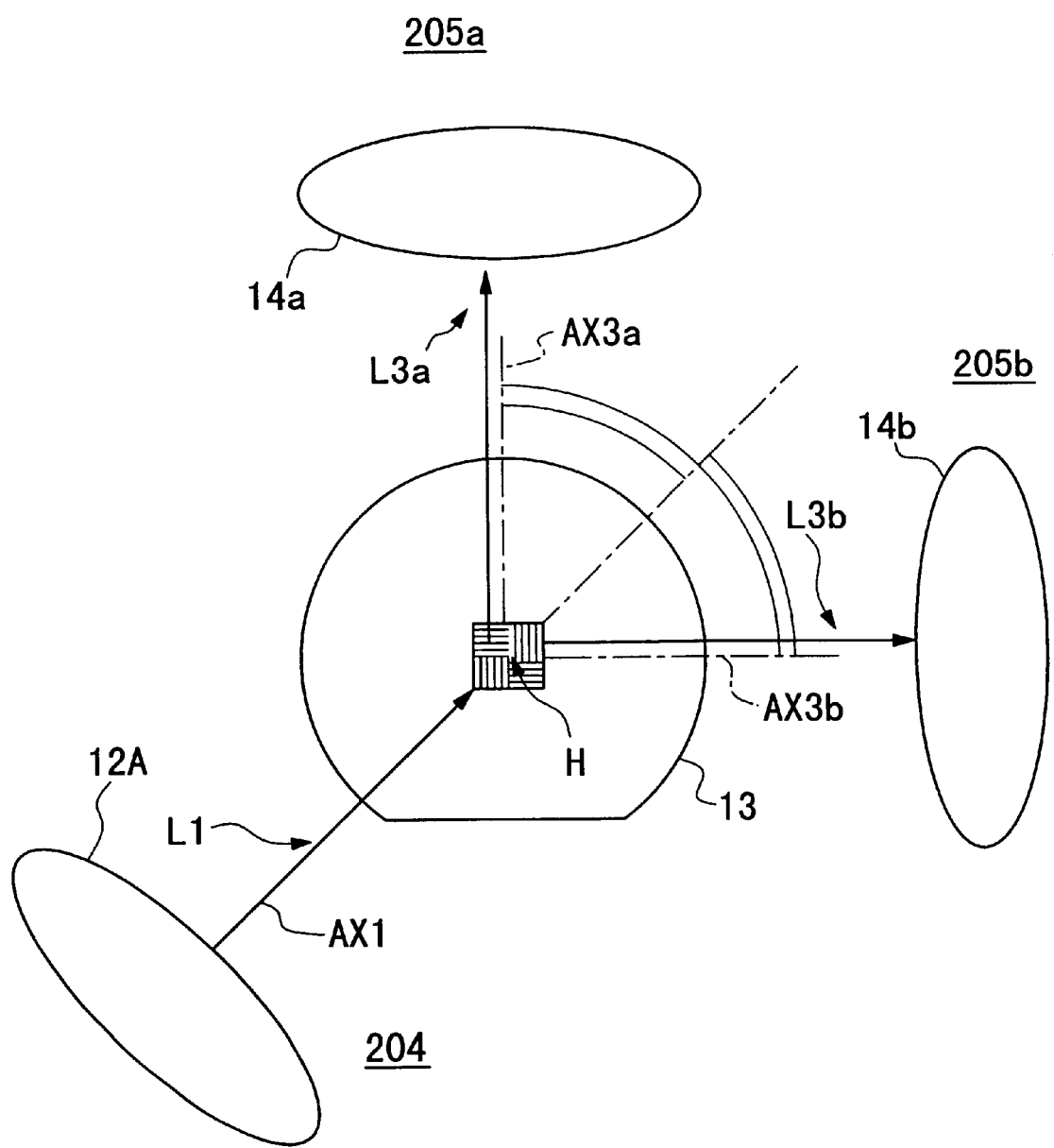
FIG. 11 is a top view of the surface inspection apparatus of FIG. 10.

A fourth embodiment of the present invention is described with reference to FIGS. 10 and 11. FIG. 10 is a perspective view of an apparatus of the fourth embodiment, and FIG. 11 is a plan view of the apparatus of FIG. 10 viewed from directly above the substrate 3.

This embodiment shows an example for a case in which the directions of repeating patterns differ. In this embodiment, a light reception optical system is provided which corresponds with the direction of each pattern, namely with the direction of each diffracted light beam. An illumination optical system 204 is provided for illuminating a substrate 13 such as a wafer, which is mounted on a substrate stage not shown in the diagrams. The illumination optical system 204 incorporates a concave mirror 12A which functions as an illumination condenser mirror and which is positioned to enable the irradiation of the illuminating light beam at a predetermined incident angle $\theta i$ with respect to the substrate 13, and a light source 11A which produces substantially monochromatic light and which is positioned at the focal plane of the mirror 12A. The light source 11A can be either a monochromatic or white light source for which the wavelength can not be altered, or a wavelength variable light source such as the light source 1 described above.

The light beam generated from the light source 11A is converted to a substantially parallel light beam L1 by the illumination condenser mirror 12A and is irradiated on to the substrate 13 at an incident angle of $\theta i$. In FIG. 10 the letter H represents the normal line of the substrate surface.

The following is a description of the construction of the light reception apparatus. As shown in the plan view of FIG. 11, in the present embodiment, the light reception optical system 205a and the light reception optical system 205b are positioned so that the respective optical axes thereof AX3a, AX3b are substantially symmetrical with respect to the optical axis AX1 of the illumination optical system 204. In the plan view of this embodiment, the optical axes AX3a and AX3b are each 45° from the optical axis AX1. Positioning the light reception optical systems in this manner enables the inspection of repeating orthogonal patterns such as those often used on semiconductor wafers. Thus, as shown in FIG. 11, if the lines of orthogonal line and space patterns for example, are placed orthogonally with respect to the optical axes of the respective light reception optical systems, then the diffracted light from each pattern will be directed to the corresponding light reception optical system.

The light reception optical system 205a is constructed in an identical manner to the light reception optical system 202 of the embodiment shown in FIG. 9. Thus, the first light reception optical system 205a for receiving the diffracted light from one pattern comprises a concave mirror 14a which functions as a light reception mirror and which is positioned at an angle of 45° relative to the traveling direction of the incident light L1 and at a diffraction angle $\theta 3n$ relative to the normal line H of the substrate 13 as shown in FIG. 10; a diaphragm 15a which is provided in the vicinity of the pupil for the light reception mirror 14a in the traveling direction of reflected light from the mirror 14a; an imaging lens 16a which is provided in the traveling direction of light which has passed through the diaphragm 15a; and an image pickup device 17a such as a CCD which is provided at a conjugate position with the surface of the substrate 13 with respect to the light reception mirror 14a and the imaging lens 16a. Furthermore, the substrate 13 possesses a swing angle with respect to the optical axis of the light reception optical system 205a. Therefore, it is preferable for the image pickup device 17a to be positioned with a swing angle sufficient to satisfy the Shineproof condition, as was the case for the embodiment of FIG. 9.

In exactly the same manner, the second light reception optical system 205b for receiving the diffracted light from the other pattern is arranged symmetrically with respect to the light reception optical system 205a. It comprises a concave mirror 14b which functions as a light reception mirror and which is positioned at a diffraction angle $\theta 3n$; a diaphragm 15b which is provided in the vicinity of the pupil for the light reception mirror 14b; an imaging lens 16b which is provided in the traveling direction of light which has passed through the diaphragm 15b; and an image pickup device 17b which is provided at a conjugate position with the surface of the substrate 13 in a position which satisfies the Shineproof condition.

With such a construction, the diffracted light which is generated in the first direction from the repeating pattern formed on the surface of the substrate is converged on to the light reception mirror 14a, and from the thus produced reflected light, only the diffracted light of a predetermined diffraction angle is selected by the diaphragm 15a and is subsequently converted by the imaging lens 16a to a first diffraction image of the substrate 13 on the imaging surface 17a. Similarly, the diffracted light which is generated in the second direction from the repeating pattern formed on the surface of the substrate is converged on to the light reception mirror 14b From the thus produced reflected light, only the diffracted light of a predetermined diffraction angle is selected by the diaphragm 15b and this is subsequently converted by the imaging lens 16b to a second diffraction image of the substrate 13 on the imaging surface 17b. By comparison of the two diffraction images with the images of a defect free substrate already stored in the image processing apparatus 18a, 18b, any foreign matter adhered to the surface of the wafer 13, scratches on the wafer surface, or irregularities in the pattern are detected, and the results are processed as substrate defect data by a computer 19 in the same manner as described for the first embodiment.

In order to ensure that images of sufficient light intensity are produced at the two diffraction directions from the repeating pattern formed on the surface of the substrate 13, as detailed above, the incident surface of the incident light should preferably incorporate the median line of the two diffraction directions as well as the normal line of the surface of the substrate 13, and furthermore, as shown in the plan view of FIG. 11, the illumination optical system should preferably produce an incident light beam at an angle of 45° relative to the pattern.

The light reception optical systems 205a, 205b should preferably be configured so that a tilt adjustment mechanism, which is not shown in the diagrams, is used to set the apparatus at the direction of the corresponding diffraction angle θ3n of the pattern.

Furthermore, in the above description the patterns differed only in direction and had identical pitch, but of course the embodiment can also be used in the case of different pitches, or in the case of examining diffracted light of different orders such as one diffracted light beam of order n and another of order (n+1), in which case the diffraction angles would be θ3n, θ3n (not shown in the diagram) and the directions of the respective light reception optical systems would be set accordingly.

The present embodiment can be used effectively for the inspection of different directions such as substrates which possess regions of repeating patterns which have a crosswise periodicity. This embodiment enables the simultaneous inspection of the patterns of two directions, and so enables a greater device manufacture throughput.

[Fifth Embodiment]

Figure 12:
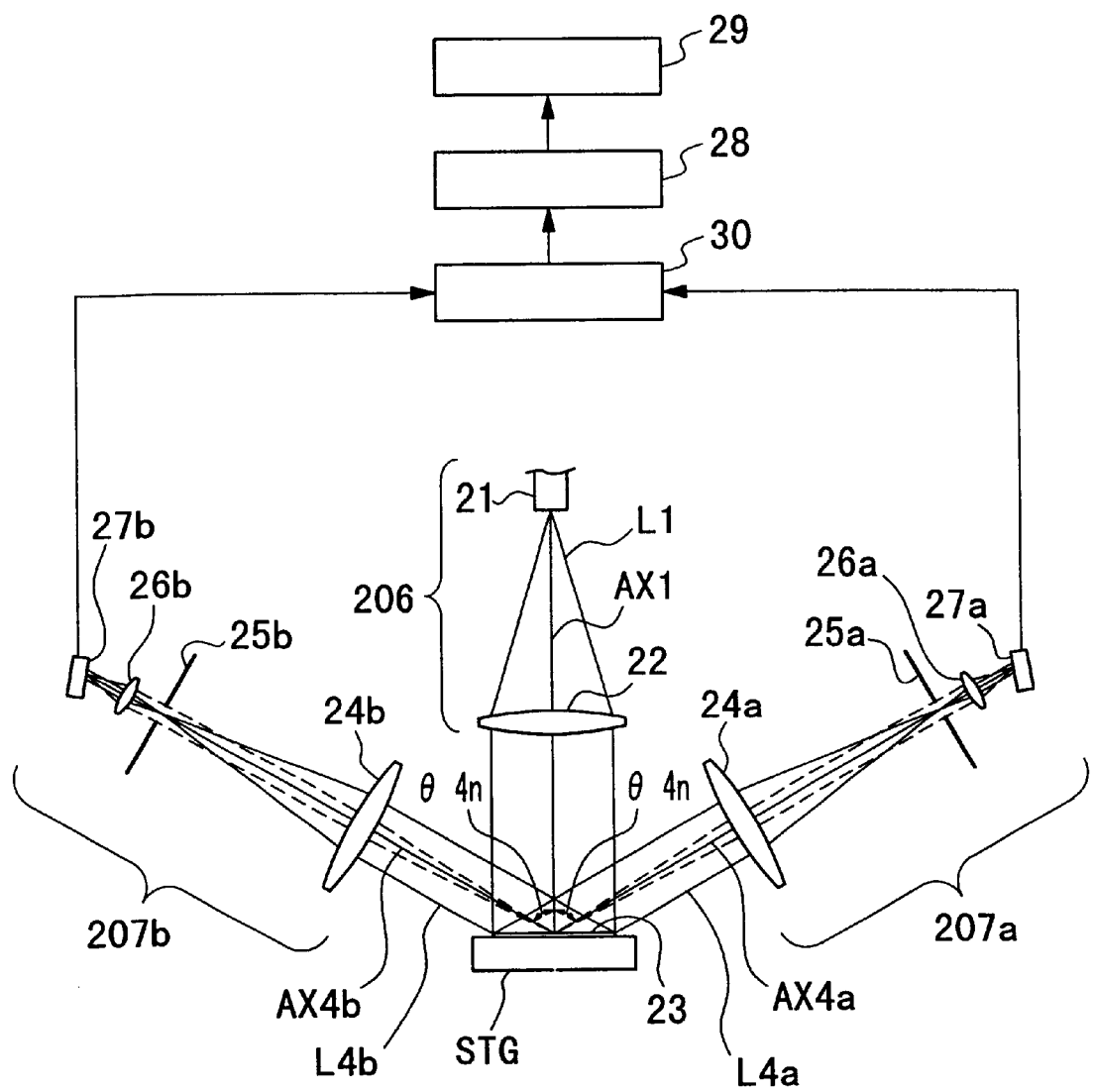
FIG. 12 is a side view showing a schematic representation of a surface inspection apparatus of yet another embodiment of the present invention.

FIG. 12 shows a fifth embodiment of the present invention. This embodiment is an example of an apparatus which is able to perform inspections of substrates on which patterns possessing asymmetry are formed, and this is done by ignoring any irregularities in the pattern so that asymmetry which does not pose a problem in processing is not detected as a defect.

In FIG. 12, an illumination optical system 206 is provided for illuminating a substrate 23 such as a wafer which is mounted on a substrate stage STG. The illumination optical system 206 incorporates an illumination condenser lens 22 which is positioned so as to irradiate an illuminating light beam from directly above the substrate 23, and a light source 21 which generates substantially monochromatic light and which is provided at the focal plane of the condenser lens 22.

The beam of light generated from the light source 21 is converted to an approximately parallel light beam by the illumination condenser lens 22 and is then irradiated on to the substrate 23 at an incident angle of 90°, namely in the direction of the normal line.

A light reception optical system 207a and a light reception optical system 207b are positioned so that the respective optical axes thereof AX4a, AX4b are substantially symmetrical with respect to the optical axis AX1 of the illumination optical system 206 (and with respect to the normal line H of the substrate 23).

A substrate can be placed on an apparatus of this type of construction so that the lines of a line and space pattern for example are positioned orthogonally to the optical axes of the respective light reception optical systems, and consequently diffracted light of the same order generated from the pattern will be directed towards each of the light reception optical systems.

The light reception optical systems 207a, 207b are constructed in the same manner as the light reception optical system 202 of the embodiment shown in FIG. 1, but convex lenses are used instead of the concave mirrors. That is, in FIG. 12, the first light reception optical system 207a for receiving diffracted light of order n from the pattern comprises a convex lens 24a which functions as a light reception lens and which is positioned at a diffraction angle of θ4n relative to the normal line H of the substrate 23 as shown in FIG. 12; a diaphragm 25a which is provided beyond the light reception lens 24a in the vicinity of the pupil therefor; an imaging lens 26a which is provided in the traveling direction of light which has passed through the diaphragm 25a; and an image pickup device 27a such as a CCD which is provided at a conjugate position with the surface of the substrate 13 with respect to the light reception lens 24a and the imaging lens 26a. It is preferable for the image pickup device 27a to be positioned with a swing angle sufficient to satisfy the Shineproof condition.

The light reception optical system 207b is positioned symmetrically with respect to the light reception optical system 207a, and is constructed in an identical manner, so the description is omitted here.

The image pickup devices 27a, 27b are connected electrically to an adding machine 30. The adding machine 30 is further connected electrically to an image processing system 28 and a computer 29.

As follows is a description of the operation of the present embodiment. A light beam generated from the light source 21 is converted to a substantially parallel beam of light by the illumination condenser lens 22, and is then used to illuminate a substrate 23 from a substantially perpendicular position. The diffraction angle θ4n of diffracted light of order n corresponding to the pattern pitch p on the substrate 23 is represented by the following formula.

$$\sin \theta 4n = \lambda/p$$

In such a case, because the illumination is perpendicular, the diffracted light of order n will be generated in both positive and negative directions. The light reception optical systems 207a, 207b, the constructions of which are described above, are positioned so that the incident angles thereof are set at the diffraction angles of plus θ4n and minus θ4n respectively, in order to capture each of the diffracted light beams. The light reception optical systems 207a, 207b converge the respective diffracted light beams via the convergent lenses 24a, 24b, select the diffracted light using the diaphragms 25a, 25b respectively, and subsequently convert the diffracted light using the imaging lenses 26a, 26b into respective images of the diffracted light of the substrate 23 on the light reception surfaces of the image pickup devices 27a, 27b respectively.

Following conversion by the respective image pickup device into an image signal proportional with the optical intensity, and subsequent correction so that each pixel of the respective image signals can be observed at the same point on the substrate, each pixel is combined using the adding machine 30 and becomes the wafer image signal.

This wafer image signal is compared with the image signal of a defect free substrate already stored in the image processing system 28 and any foreign matter adhered to the surface of the substrate 23, scratches on the substrate surface, or irregularities in the pattern are detected and then collated as substrate defect data by the computer 29.

Figure 13:
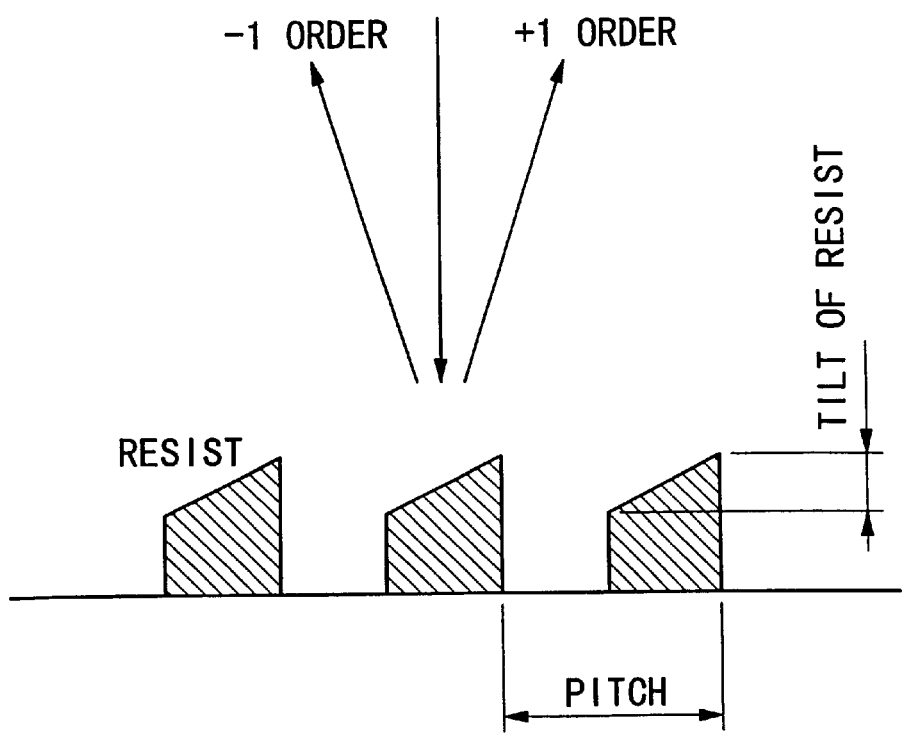
FIG. 13 is a sectional side elevation of the resist section of a substrate for describing the principles of yet another embodiment of the present invention.
Figure 14:
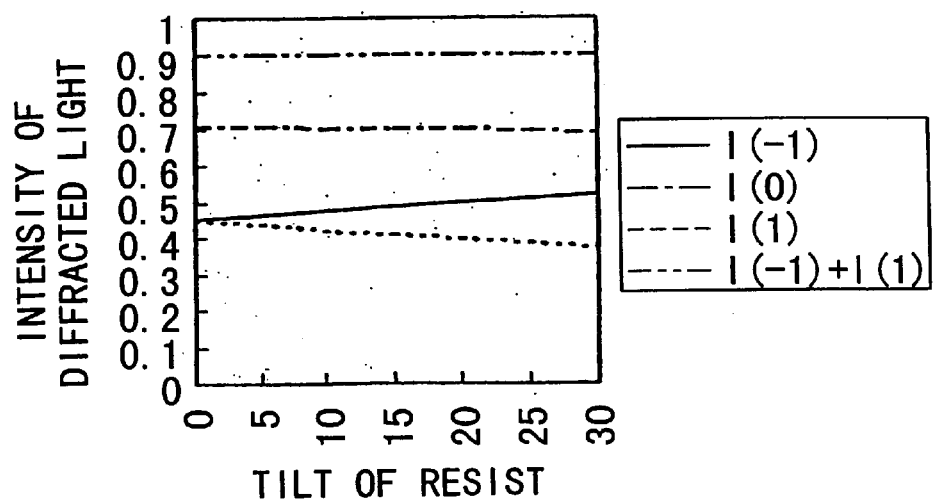
FIG. 14 is a line diagram showing the relationship between the tilt of the resist layer and the intensity of diffracted light.

When the upper surface of the resist coating applied to the top of the substrate 23 is tilted as shown in FIG. 13, the light intensity of diffracted light of order ±1 is shown in FIG. 14. It is evident that the intensity of the diffracted light of the tilted direction increases, while the intensity of the opposite diffracted light beam decreases.

This condition is known as "blazed". The intensity of the diffracted light is such that the plus 1 diffracted light and the minus 1 diffracted light offset one another, so it is clear that that by taking the sum of the light intensities of the light of order ±1, the optical intensity will be a substantially constant value even if blazed. Consequently, by obtaining the sum of these type of light intensities, an inspection can be carried out without the detection of irregularities in the surface which result from minor irregularities in the thickness of the resist coating.

[Sixth Embodiment]

Figure 15:
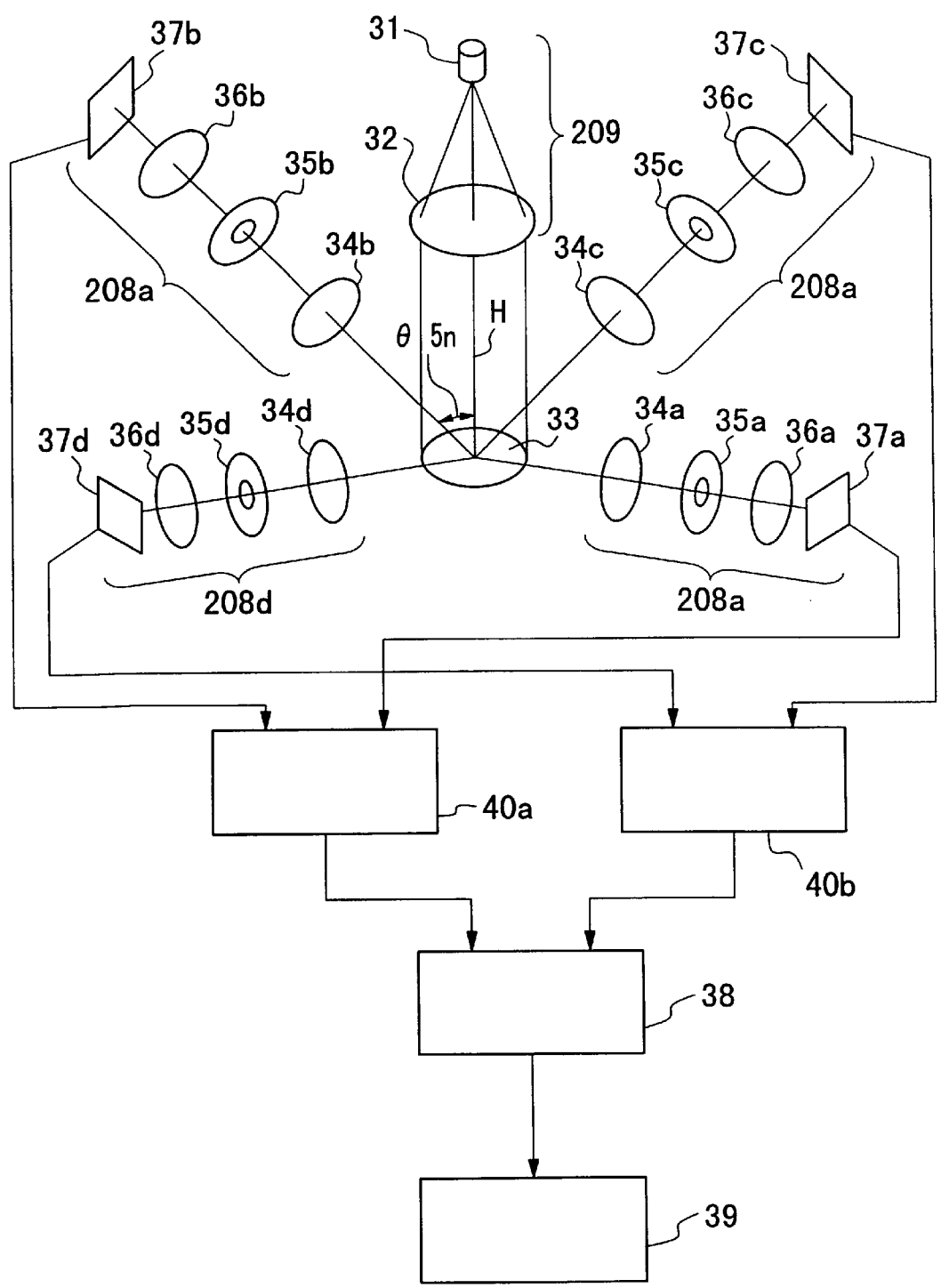
FIG. 15 is a perspective view showing a schematic representation of a surface inspection apparatus of yet another embodiment of the present invention.

A sixth embodiment generated by combining the fourth embodiment and the fifth embodiment is shown in FIG. 15. This embodiment is particularly suitable for the inspection of ASICs.

In FIG. 15, an illumination optical system 209 for illuminating a substrate 33 is constructed in an identical manner to the illumination optical system 206 shown in FIG. 12. That is, the illumination optical system 209 incorporates an illumination condenser lens 32 which is positioned so as to irradiate an illuminating light beam from directly above the substrate 33, and a light source 31 which generates substantially monochromatic light and which is provided at the focal plane of the condenser lens 32. The operation of the illumination optical system 209 is also identical with that of the illumination optical system 206 and so the description is omitted here.

Light reception optical systems 208a, 208b, 208c, and 208d are constructed in the same manner as the light reception optical system 207a. Thus, each comprise a convex lens 34a, 34b, 34c, 34d which functions as a light reception lens and which is positioned at a diffraction angle of θ5n; a diaphragm 35a, 35b, 35c, 35d which is provided beyond the light reception lens 34a, 34b, 34c, 34d in the vicinity of the pupil therefor; an imaging lens 36a, 36b, 36c, 36d which is provided in the traveling direction of light which has passed through the diaphragm 35a, 35b, 35c, 35d; and an image pickup device 37a, 37b, 37c, 37d such as a CCD which is provided at a conjugate position with the surface of the substrate 33 with respect to the light reception lens and the imaging lens. As was the case for the previous embodiment, it is preferable for each image pickup device to be positioned with a swing angle sufficient to satisfy the Shineproof condition.

The light reception optical systems 208a, 208b and the light reception optical systems 208c, 208d are each positioned symmetrically with respect to the normal line H.

The image pickup devices 37a, 37b are connected electrically to an adding machine 40a, and the image pickup devices 37c, 37d are connected electrically to an adding machine 40b. The adding machines 40a, 40b are further connected electrically to an image processing system 38 and a computer 39.

A substrate can be placed on an apparatus of this type of construction so that the lines of two line and space patterns for example are positioned orthogonally to the optical axes of the respective light reception optical systems, and consequently diffracted light of the same order generated from the pattern will be directed towards each of the symmetrically positioned light reception optical systems. Typically, the two line and space patterns will be orthogonal, and so the four light reception optical systems will be positioned at equal 90° intervals around the normal line H.

Thus a combination of light reception optical systems 208a and 208b, and light reception optical systems 208c and 208d can be viewed as a combination of two apparatus of the fifth embodiment, while a combination of light reception optical systems 208a and 208c, and light reception optical systems 208b and 208d can be viewed as a combination of two apparatus of the fourth embodiment. The operation of the combinations will be as described for the respective embodiments.

In this manner, it is possible to perform a simultaneous inspection of the periodic patterns of two directions without the detection of irregularities in the surface which result from minor irregularities in the thickness of the resist coating and even in the case of blaze. Consequently, this embodiment enables the simultaneous inspection of two directions without picking up as defects minor irregularities which do not pose a problem in processing, and so is able to generate a marked improvement in device manufacture throughput.

As described above, with a surface inspection apparatus of the present invention, inspections of patterned objects can be performed reliably and with a high throughput level to detect foreign matter adhered to, or scratches on the surface of the object as well as abnormalities such as abnormalities in the pattern line width or irregularities in the pattern, and consequently the apparatuses are very suitable for the inspection of semiconductor wafers such as memory wafers, and semiconductor devices such as liquid crystal display panels.

With the fifth and sixth embodiments, suitable inspections can be carried out with no increase in time, not only on objects such as memory which up until now have had elements formed uniformly over the entire surface of the wafer, but also on objects such as CPUs and ASICs in which the pitch forming the elements can be different. The fifth and sixth embodiments are able to detect foreign matter adhered to a substrate, scratches on the substrate surface, or abnormalities in the pattern, without detecting minor irregularities in the resist coating which will not effect processing.

Furthermore, in each of the embodiments, in order to suppress variation in the size of the image produced on the screen of the image pickup device such as a CCD, it is preferable for the substrate to be positioned at the front focal point of the light reception lens or light reception mirror, and for the diaphragm to be positioned at the rear focal point of the light reception lens or light reception mirror and moreover at the front focal point of the imaging lens, producing a two-sided telemetric optical system.

[Surface Inspection Method Embodiment]

In the following, a description of an embodiment of the surface inspection method of the present invention is explained. An illuminating light beam L1 is irradiated on to a substrate (surface). Diffracted light of a first direction generated at the surface is received by a first light reception optical system, and diffracted light of a second direction generated at the surface is received by a second light reception optical system. An image of the surface resulting from the diffracted light of the first direction is formed on an image pickup device and undergoes image processing at a first image processing apparatus. Similarly, an image of the surface resulting from the diffracted light of the second direction is formed on a different image pickup device and undergoes image processing at a second image processing apparatus. The thus obtained image information relating to the surface is sent to a computer which functions as a central computing device, where the condition of the surface, including defects for example, is detected by comparison with a reference image. The two sets of information can also be integrated, that is superimposed, and used as a mutual correction tool, so that when an image condition from one image suggests the possibility of a defect, the other image is used to confirm whether or not the defect is real. For example, by superimposing the images and adding and subtracting the two sets of information, conditions on the surface can be detected which could not be identified from a single set of information. The two sets of information can also be handled simultaneously enabling an improvement in the inspection throughput.

As shown in FIG. 9, in the case where two types of pattern with the same direction but different pitch are formed on a substrate 3, the diffracted light beam L2a of the first direction and the diffracted light beam L2b of the second direction each correspond with a respective pitch. The beams are diffracted light beams of the same order but with different diffraction angles. In this manner, information from two types of diffracted light can be obtained at one time, thus increasing the inspection throughput. Furthermore, by using integrated or superimposed processing of the information at a single computing device, highly reliable inspections are possible.

As shown in FIGS. 10 and 11, in the case where two types of pattern of different directions are formed on the substrate 13, the diffracted light beams L3a and L3b have diffraction angles of the same magnitude which correspond with the respective pattern directions, and are diffracted light beams of the same order but different directions about the normal line H of the substrate. Particularly for the inspection of substrates in which the patterns are positioned at right angles, the first and second directions will be perpendicular to one another. In this manner, information relating to the patterns of two directions can be obtained simultaneously, thus increasing the inspection throughput.

As shown in FIG. 12, in the case where the illuminating light beam is irradiated perpendicularly on to the substrate 23, the diffracted light beams L4a and L4b are generated in symmetrical directions and are of the same order, for example, a light beam of order plus 1 and a light beam of order minus 1. Because diffracted light beams of symmetrical directions are detected, inspections can be performed without the detection of irregularities in the surface resulting from factors such as minor irregularities in the thickness of the resist coating. Thus, because minor defects which are insufficient to constitute a problem product are not detected, an improvement in manufacturing throughput can be achieved.

In the above inspection method, constructions were described in which a first light reception optical system receives a diffracted light beam of a first direction, and a second light reception optical system receives a diffracted light beam of a second direction, but both the first light reception optical system and the second light reception optical system could also be set to capture scattered light from the pattern.

[Seventh Embodiment]

Figure 16:
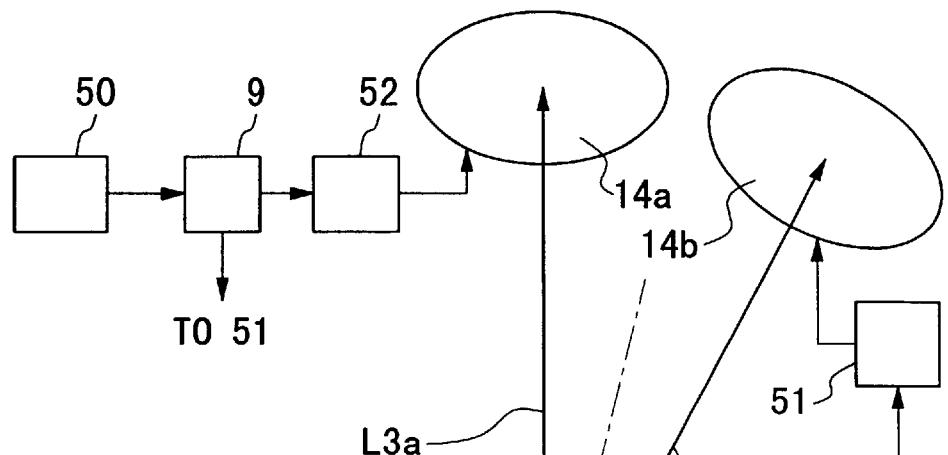
FIG. 16 is a plan view from above of a surface inspection apparatus of yet another embodiment of the present invention.

In the following, a description of a seventh embodiment of the present invention is explained with reference to FIG. 16. In FIG. 16, those members which possess the same function as in FIGS. 10 and 11 are labeled with the same reference numbers.

In elements such as memory, repeating patterns are often lined up orthogonally, but depending on the shape of the pattern, the directions in which diffracted light is generated are not necessarily orthogonal. For example, in the pattern shown in FIG. 17, where the pattern is formed by the intersection of a plurality of first parallel linear groups with a plurality of second parallel linear groups at an angle other than 90° (specifically in a pattern which is shaped like the loop shaped rotating hand grip of an escalator viewed directly from the side thereof), the diffracted light beams will not be generated in orthogonal directions, and can be generally assumed to be generated in directions orthogonal to the straight line sections of the pattern.

In order to capture this diffracted light, a light illumination system 11A~12A (the light source 11A is not shown in the diagram), and light reception systems 14a~17a (only the concave mirror 14a is shown in the diagram) and 14b~17b (only the concave mirror 14b is shown in the diagram) need to be positioned in the locations shown in FIG. 16 (in FIG. 11 the optical axes of the two light reception optical systems were positioned at right angles, but in this embodiment the positioning results in an acute angle).

In this case, it is preferable to provide drive units for at least the two light reception systems 14a~17a, 14b~17b, or alternatively in the light illumination system 11A~12A and the light reception system 14b~17b. For example, as shown in FIG. 16, drive units 51 and 52 may be provided respectively for the light reception system 14b~17b and the light reception system 14a~17a. Instead, it is also possible to provide drive units 51 and 52' respectively for the light reception system 14b~17b and the light illumination system 11A~12A. In these cases, it is possible to move the light illumination system 11A~12A and the light reception systems 14a~17a, 14b~17b with regard to one another in accordance with the direction of the generated diffracted light which will correspond with the shape of the pattern (FIG. 17) formed on the substrate 13.

With this embodiment, a computer 9 is connected to the drive sections 51, 52 (or 52') and is configured to also function as a control device for controlling the drive amount for the drive systems (51, 52, or alternatively 51, 52'). Furthermore, an input device 50 is also connected to the computer 9 which enables the input of process information into the computer 9.

Figure 17:
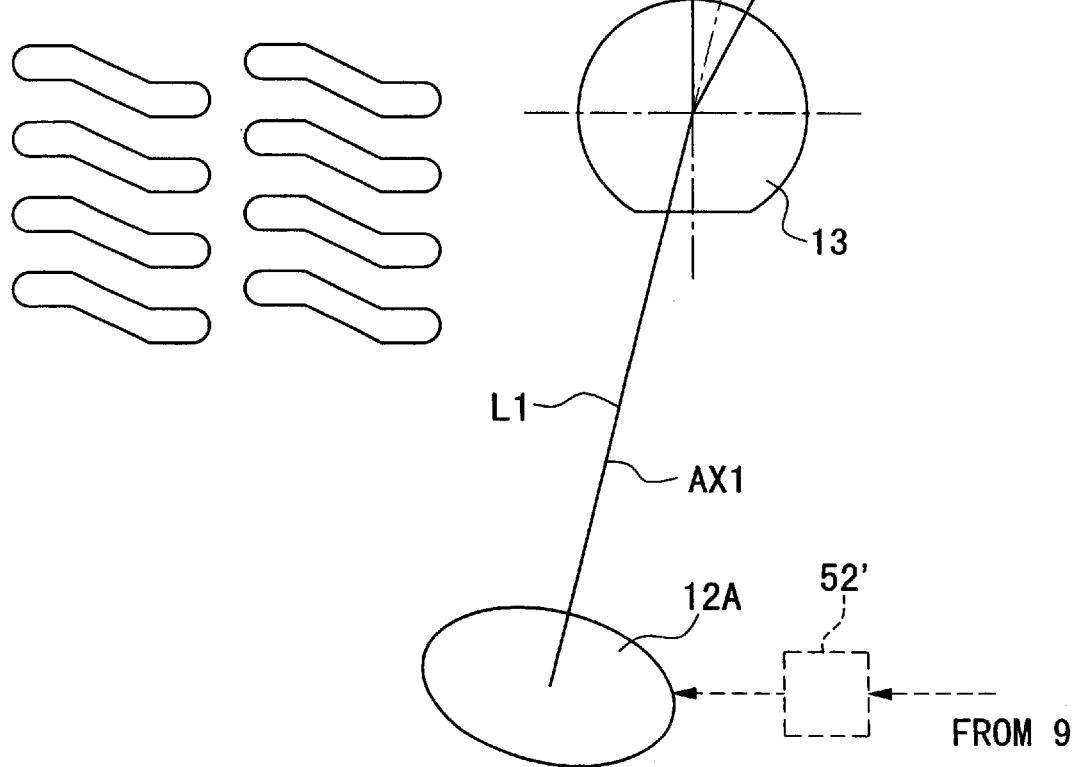
FIG. 17 is a plan view showing the structure of a pattern of a body.

By driving the computer 9 controlled drive sections in this manner, the optical axis of the light reception system 14a~17a of FIG. 16 is adjusted to a direction orthogonal to the line portion of the first linear group of the pattern of FIG. 17, and the optical axis of the light reception system 14b~17b is adjusted to a direction orthogonal to the line portion of the second linear group of the pattern of FIG. 17. Furthermore, the optical axis of the light illumination system 11A~12A thus becomes the direction which equally divides the optical axes of the two light reception systems.

The positions for inspections of the various process wafers are determined in advance, and then upon inspection the appropriate process information is input into the input device 50, and the computer 9 then adjusts the positioning of the light reception systems and light illumination system via the drive systems (51, 52 or 51, 52') in accordance with the input information.

Alternatively, the computer could also scan (move) the light reception systems using the drive systems (51, 52 or 51, 52') to determine the position where the signal from the CCD 17a, 17b is greatest, and capture the image at the position where the intensity of the diffracted light is greatest, and then perform the inspection by adjusting the rotation of the image with a signal processing system.

Although not described above, a wavelength variable light source such as that of the first and second embodiments can also be applied to the light source used in the third~seventh embodiments. By using a wavelength variable light source similar to the light source 1 of the first and second embodiments as the light source for embodiments 3~7, the following types of macro inspections can be carried out.

By making the wavelength λ of the light source variable, the first and second light reception optical apparatus are able to receive various types of light with the illumination angle, the surface angle of the object and the light reception angle all held at fixed values. The types of light include diffracted light (incorporating diffracted light of different orders) and scattered light. Taking the third embodiment as an example, the wavelength ; of the light source can be set so that the first light reception optical system 202 and the second light reception optical system 203 are able to receive scattered light generated from patterns of different pitch. Furthermore, it is also possible to alter the order of the diffracted light received by the first light reception optical system 202 to (n+1) and to alter the order of the diffracted light received by the second light reception optical system 203 to (n+2), and the capture by each light reception optical system of diffracted light beams of even higher orders is also possible. Moreover, the wavelength λ of the light source can also be set so that for inspection of a single pitch pattern, one of either the first light reception optical system 202 or the second light reception optical system 203 receives diffracted light, while the other optical system receives scattered light.

A plurality of embodiments are described above, but the present invention is in no way limited to only these embodiments, and combinations of the configurations of each embodiment are also possible, as are combinations of each embodiment with conventional configurations.

Furthermore in the above descriptions, wafers were used as the objects, but, for example, the present invention is also very suitable for the macro inspection of square substrates on which liquid crystal element patterns are formed.

Moreover in the above descriptions the surface inspection of an entire wafer surface was used as an example, but, for example, it is also possible to assign one chip region or one shot region as the region to undergo inspection, and the assignment of a plurality of chip regions or a plurality of shot regions as regions for inspection is also possible.

Furthermore, the illumination optical systems and the light reception optical systems were each constructed of a reflection optical system using a concave mirror, but the illumination optical systems and the light reception optical systems could also be constructed of refraction optical systems using optical lenses, or catadioptric systems using a combination of reflective mirrors and optical lenses.

The manufacture of a surface inspection apparatus of an embodiment of the present invention is carried out by integrating the illumination optical system and the light reception optical systems, which are constructed of a plurality of optical elements (such as concave mirrors), into the main body of the surface inspection apparatus, carrying out optical adjustments as well as adjusting the position of, and then attaching, the light source, wavelength selection filter, and the image pickup device to either the illumination optical system or the light reception optical system and then attaching the associated wiring and piping, and then performing overall adjustments (such as electrical adjustments and operational checks). It is preferable for the manufacture of the surface inspection apparatus to be performed in a clean room where the temperature and level of cleanliness is controlled.

INDUSTRIAL APPLICABILITY

The present invention relates to technology for the surface inspection of substrates used in the manufacture of liquid crystal devices or the semiconductor wafers used in the manufacture of ICs, and in particular relates to an apparatus and method for performing so-called macro inspections in which the entire surface of the object is examined. With the apparatus of the present invention, macro inspections can be carried out efficiently on a variety of objects while apparatuses such as the illumination apparatus and the image projection apparatus are maintained in fixed positions. Furthermore, highly reliable inspections are achievable regardless of the condition of the surface.

What is claimed is:

1. A surface inspection apparatus comprising:
    an illumination apparatus which is fixed in a position facing an object at a first predetermined angle with respect to the object and which irradiates an illuminating light beam toward an inspection region of the object, wherein a wavelength of the illuminating light beam can be varied;
    an image pickup device which is fixed in a position facing the object at a second predetermined angle with respect to the object and which receives diffracted light or scattered light generated from the illumination of the object by the illuminating light beam and creates an image of the object; and
    an image processing apparatus which takes an image signal obtained by the image pickup device and performs a macro inspection of the inspection region by carrying out image processing;
    wherein the illumination apparatus is capable of altering or selecting at least two wavelengths including a first wavelength and a second wavelength, if the first predetermined angle is represented by an angle of θi with respect to a line perpendicular to the surface of the object and the second predetermined angle is represented by an angle of θd with respect to the line perpendicular to the surface of the object, then the first wavelength is a wavelength ), which is set so as to satisfy the following formula:

$(\sin\theta i - \sin\theta d) = n \cdot \lambda 1 / p$ (n: order of diffracted light undergoing image projection, p: pattern pitch of the surface of the object),
    and the second wavelength is a wavelength λ2 which is set such that an angle θd' which is determined by the following formula:

$(\sin\theta i - \sin\theta d') = n \cdot \lambda 2 / p$ (n: order of diffracted light generated from the illuminating light beam, p: pattern pitch of the surface of the object), and an angle θd" which is determined by the following formula:

$$(\sin\theta i - \sin\theta d'') = (n+1) \cdot \lambda 2/p$$

satisfy the requirement that $$\theta d' < \theta d < \theta d''.$$

2. A surface inspection apparatus according to claim 1, wherein the illumination apparatus includes a light source and an optical member which converts light from the light source into a substantially parallel light beam, and wherein a wavelength alteration member is positioned between the light source and the optical member.

3. A surface inspection apparatus according to claim 2, wherein the wavelength alteration member is a wavelength selection filter.

4. A surface inspection apparatus according to claim 2, wherein the wavelength alteration member is a diffraction grating.

5. A surface inspection apparatus according to claim 2, wherein the wavelength alteration member is a spectral prism.

6. A surface inspection apparatus according to claim 2, wherein the optical member is constructed from a concave mirror, and the light source is positioned at a focal point of the concave mirror.

7. A surface inspection apparatus according to claim 1, wherein the illumination apparatus comprises a wavelength variable light source, and an optical member which converts light from the wavelength variable light source into a substantially parallel light beam.

8. A surface inspection apparatus according to claim 1, wherein the image pickup device comprises a concave mirror which converges the diffracted light or scattered light from the object and an image pickup element which produces and picks up the image of the object from the diffracted light or scattered light converged by the concave mirror.

9. A surface inspection apparatus according to claim 1, wherein the illumination apparatus comprises a linear diffuse light source and a cylindrical lens positioned facing along a line of the linear diffuse light source, and wherein the cylindrical lens generates a light beam from the light from the linear diffuse light source which is substantially parallel in at least one direction and then illuminates the object.

10. A surface inspection apparatus according to claim 1, further comprising:

a second image pickup device which is fixed in a position facing the object at a third predetermined angle with respect to the object and which receives diffracted light or scattered light generated from the illumination of the object by the illuminating light beam and picks up an image of the object, and a second image processing apparatus which is connected to the second image pickup device and which takes an image signal obtained by the second image pickup device and performs a macro inspection of the object by carrying out image processing.

11. A surface inspection apparatus according to claim 10, further comprising a central computing apparatus, which is connected to the image processing apparatus and the second image processing apparatus and which judges a surface condition of the inspection region by processing information obtained from the image processing apparatus and the second image processing apparatus.

12. A surface inspection apparatus comprising:

a first light reception optical system, which is positioned at a predetermined location with respect to an object, and which receives a first light from the object;

a second light reception optical system, which is positioned in a different location than the first light reception optical system, and which receives a second light from the object;

a first image processing apparatus, which is positioned in a location to receive the first light from the first light reception optical system, and which processes an image of the surface of the object obtained by the first light reception optical system;

a second image processing apparatus, which is positioned in a location to receive the second light from the second light reception optical system, and which processes an image of the surface of the object obtained by the second light reception optical system; and a central computing apparatus, which is connected to the first image processing apparatus and the second image processing apparatus, and which detects a condition of the surface of the object;

wherein one of the first light reception optical system and the second light reception optical system receives light of a wavelength λ such that an angle of θd' which is determined by the following formula:

$$(\sin\theta i - \sin\theta d) = n \cdot \lambda/p$$

(n: order of diffracted light undergoing image projection, p: pattern pitch of the surface of the object)

or by the formula:

$$(\sin\theta i - \sin\theta d') = n \cdot \lambda/p$$

(n: order of diffracted light generated from the illuminating light beam, p: pattern pitch of the surface of the object), and an angle of θd" which is determined by the following formula:

$$(\sin\theta i - \sin\theta d'') = (n+1) \cdot \lambda/p$$

satisfy the requirement that $$\theta d' < \theta d < \theta d''.$$

13. A surface inspection apparatus according to claim 12, wherein the optical axes of the first and second light reception optical systems are positioned to be substantially symmetrical with respect to an optical axis of an illumination optical system.

14. A surface inspection apparatus according to claim 12, wherein to enable reception by the first and second light reception optical systems of the diffracted light generated in accordance with the structure of a body which is positioned on the object, the surface incorporating the optical axis of the first light reception optical system and a normal line of the object intersects with the surface incorporating the optical axis of the second light reception optical system and the normal line of the surface of the object.

15. A surface inspection method comprising:

an illuminating step of irradiating an illuminating light beam, which has been adjusted by a wavelength selecting device and a parallel light beam converting device, toward an inspection region of an object;

a light reception step of receiving a diffracted light or a scattered light generated from the object by a light reception apparatus fixed in a position facing the object at a second predetermined angle with respect to the object;

an image processing step of processing an image of the object obtained in the light reception step; and detecting a condition of a surface of the object by processing information obtained in the image processing step;

wherein the wavelength selecting device selects a wavelength of the illuminating light beam of an illumination apparatus fixed in a position facing the object at a first predetermined angle with respect to the object such that the wavelength satisfies at least the formula:

$$(\sin\theta i - \sin\theta d) = n \cdot \lambda / p$$

(n: order of diffracted light undergoing image projection, p: pattern pitch of the surface of the object)

or such that an angle of θd' which is determined by the following formula:

$$(\sin\theta i - \sin\theta d) = n \cdot \lambda / p$$

(n: order of diffracted light generated from the illuminating light beam, p: pattern pitch of the surface of the object), and an angle of θd" which is determined by the following formula:

$$(\sin\theta i - \sin\theta d'') = (n+1) \cdot \lambda / p$$

satisfy the requirement that $$\theta d' < \theta d < \theta d'',$$

and wherein the parallel light beam converting device converts the illuminating light beam to be light which is substantially parallel.

16. A surface inspection method according to claim 15, wherein the selecting of the wavelength of the illuminating light beam is carried out by inserting an arbitrary wavelength selection filter into an optical path of the illuminating light beam.

17. A surface inspection method according to claim 15, wherein the selecting of the wavelength of the illuminating light beam is carried out by a diffraction grating positioned in an optical path of the illuminating light beam.

18. A surface inspection method according to claim 15, wherein the selecting of the wavelength of the illuminating light beam is carried out by a spectral prism positioned in an optical path of the illuminating light beam.

19. A surface inspection method according to claim 15, wherein the selecting of the wavelength of the illuminating light beam is carried out by the use of a wavelength variable light source in a light source of the illuminating light beam.

20. A surface inspection method comprising:

an illuminating step of irradiating an illuminating light beam, which has been adjusted by a wavelength selecting device and a parallel light beam converting device, toward an inspection region of an object;

a first light reception step of receiving light of a first direction from the object by a first light reception optical system positioned at a predetermined location with respect to the object;

a second light reception step of receiving light of a second direction from the object by a second light reception optical system positioned at a different location from that of the first light reception optical system;

a first image processing step of processing an image of a surface of the object obtained in the first light reception step by a first image processing apparatus positioned at a location for receiving the first light from the first light reception optical system;

a second image processing step of processing an image of a surface of the object obtained in the second light reception step by a second image processing apparatus positioned at a location for receiving the second light from the second light reception optical system; and a computing step of detecting a condition of the surface of the object by processing information obtained in the first image processing step and the second image processing step;

wherein the wavelength selecting device alters or selects a wavelength of the illuminating light beam of an illumination apparatus fixed in a position facing the object at a first predetermined angle with respect to the object such that the wavelength satisfies at least the formula:

$$(\sin\theta i - \sin\theta d) = n \cdot \lambda / p$$

(n: order of diffracted light undergoing image projection, p: pattern pitch of the surface of the object)

or such that an angle of θd' which is determined by the following formula:

$$(\sin\theta i - \sin\theta d) = n \cdot \lambda / p$$

(n: order of diffracted light generated from the illuminating light beam, p: pattern pitch of the surface of the object), and an angle of θd" which is determined by the following formula:

$$(\sin\theta i \times \sin\theta d'') = (n+1) \cdot \lambda / p$$

satisfy the requirement that $$\theta d' < \theta d < \theta d'',$$

and wherein the parallel light beam converting device converts the illuminating light beam to be light which is substantially parallel.

21. A surface inspection method according to claim 20, wherein a line and space pattern with associated periodicity is formed on the object, and wherein the first and second directions are each substantially perpendicular to the lines of the line and space pattern.

22. A surface inspection method according to claim 20, wherein the first and second directions are the traveling directions of the diffracted light of order plus-1 and the diffracted light of order minus-1 generated from the line and space pattern, respectively.

23. A surface inspection method according to claim 20, wherein the selecting of the wavelength of the illuminating light beam is carried out by inserting an arbitrary wavelength selection filter into an optical path of the illuminating light beam.

24. A surface inspection method according to claim 20, wherein the selecting of the wavelength of the illuminating light beam is carried out by a diffraction grating positioned in an optical path of the illuminating light beam.

25. A surface inspection method according to claim 20, wherein the selecting of the wavelength of the illuminating light beam is carried out by a spectral prism positioned in an optical path of the illuminating light beam.

26. A surface inspection method according to claim 20, wherein the selecting of the wavelength of the illuminating light beam is carried out by the use of a wavelength variable light source as a light source of the illuminating light beam.

* * * * *